(12) United States Patent
Ni et al.

(10) Patent No.: US 11,666,533 B2
(45) Date of Patent: *Jun. 6, 2023

(54) EMULSION FORMULATIONS OF MULTIKINASE INHIBITORS

(71) Applicant: Cloudbreak Therapeutics, LLC, Irvine, CA (US)

(72) Inventors: Jinsong Ni, Irvine, CA (US); Van Dinh, Irvine, CA (US); Walter Tien, Irvine, CA (US)

(73) Assignee: Cloudbreak Therapeutics, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/509,774

(22) Filed: Oct. 25, 2021

(65) Prior Publication Data
US 2022/0040103 A1 Feb. 10, 2022

Related U.S. Application Data

(63) Continuation of application No. 17/272,105, filed as application No. PCT/US2019/048635 on Aug. 28, 2019.

(60) Provisional application No. 62/723,998, filed on Aug. 28, 2018.

(51) Int. Cl.
| | | |
|---|---|---|
| *A61K 31/496* | (2006.01) | |
| *A61K 47/40* | (2006.01) | |
| *A61K 47/44* | (2017.01) | |
| *A61K 9/00* | (2006.01) | |
| *A61K 9/107* | (2006.01) | |
| *A61P 27/02* | (2006.01) | |

(52) U.S. Cl.
CPC ............ *A61K 9/107* (2013.01); *A61K 9/0048* (2013.01); *A61K 31/496* (2013.01); *A61K 47/40* (2013.01); *A61K 47/44* (2013.01); *A61P 27/02* (2018.01)

(58) Field of Classification Search
None
See application file for complete search history.

(56) References Cited

U.S. PATENT DOCUMENTS

| | | |
|---|---|---|
| 9,987,223 B2 | 6/2018 | Ni |
| 2014/0378401 A1 | 12/2014 | Horn |
| 2015/0196649 A1 | 7/2015 | Horn |
| 2016/0339105 A1 * | 11/2016 | Shah ................. A61K 47/34 |
| 2019/0110984 A1 | 4/2019 | Ni |
| 2019/0290643 A1 | 9/2019 | Ni et al. |
| 2020/0323844 A1 | 10/2020 | Ni et al. |
| 2021/0315815 A1 | 10/2021 | Ni |

FOREIGN PATENT DOCUMENTS

| | | | |
|---|---|---|---|
| CN | 107028949 A * | 8/2017 | |
| WO | WO 2016/178881 | 11/2016 | |
| WO | WO-2016200688 A1 * | 12/2016 | ............ A61F 9/00 |
| WO | WO-2017210132 A1 * | 12/2017 | ........... A61K 31/365 |
| WO | WO 2018/054077 | 3/2018 | |

OTHER PUBLICATIONS

PCT International Preliminary Report on Patentability in Appln No. PCT/US2019/048635, dated Mar. 2, 2021, 8 pages.
PCT International Search Report and Written Opinion in Appln No. PCT/US2019/048635, dated Nov. 12, 2019, 13 Pages.
Extended European Search Report in European Application No. 19856131.8, dated Apr. 19, 2022, 7 pages.

* cited by examiner

*Primary Examiner* — Gigi G Huang
(74) *Attorney, Agent, or Firm* — Fish & Richardson P.C.

(57) ABSTRACT

Compositions comprising a therapeutically effective amount of a multikinase inhibitor, such as nintedanib or axitinib or pazopanib, are provided, wherein the composition is an emulsion, such as a nanoemulsion, with lipophilic carrier (e.g., castor oil), a polyoxyl oil (e.g., polyolyl-35 castor oil), optionally with a surfactant (e.g., polysorbate 80), optionally with a cyclic oligosaccharide, such as a cyclodextrin (e.g., 2-hydroxypropyl-beta-cyclodextrin), as a solubilizer. Methods for treating ocular conditions with the compositions are also provided.

9 Claims, 2 Drawing Sheets

EMULSION FORMULATIONS OF MULTIKINASE INHIBITORS

CROSS REFERENCE TO RELATED APPLICATION

This application is a continuation application of U.S. application Ser. No. 17/272,105, filed on Feb. 26, 2021, which is a National Stage Application under 35 U.S.C. § 371 and claims the benefit of International Application No. PCT/US2019/048635, filed Aug. 28, 2019, which claims the benefit of U.S. Provisional Application Ser. No. 62/723,998, filed Aug. 28, 2018, the content of which are incorporated herein by reference in their entireties.

TECHNICAL FIELD

Provided herein are formulations for delivery of multikinase inhibitors.

BACKGROUND

Multikinase inhibitors are inhibitors that target more than one protein kinases. Protein kinases are enzymes that add a phosphate group to a protein, and can modulate its function. Phosphorylation regulates many biological processes, and multikinase inhibitors can be used to treat various diseases or to modulate cellular functions. The therapeutic potential of such compounds depends, at least in part, on the extent to which the compounds can be formulated and delivered in a way that is suitable for particular treatments.

SUMMARY

Provided herein are compositions for the delivery of multikinase inhibitors. In some embodiments, compositions and methods for treating one or more ocular conditions are provided.

The disclosure provides compositions for treating ocular conditions, including diseases affecting the anterior segment of the eye diseases. The composition can comprise a therapeutically effective amount of a multikinase inhibitor, such as nintedanib or axitinib or pazopanib, wherein the composition is an emulsion, such as a nanoemulsion (e.g., comprising castor oil, polyoxyl-35 castor oil, and optionally polysorbate 80), with a cyclic oligosaccharide, such as a cyclodextrin (e.g., 2-hydroxypropyl-beta-cyclodextrin), as a solubilizer, and is suitable for topical administration to an eye. The disclosure further provides methods for treating ocular conditions with the disclosed compositions.

In some embodiments, a composition suitable for topical administration to an eye is provided comprising a therapeutically effective amount of a multikinase inhibitor, such as nintedanib or axitinib or pazopanib, wherein said composition comprises an emulsion, such as a nanoemulsion, with cyclodextrin, such as 2-hydroxypropyl-beta-cyclodextrin, as a solubilizer. In some embodiments, methods are provided for treating an ocular condition associated with angiogenesis, such as hyperemia, neovascularization, pterygium, pinguecula, glaucoma filtration surgery and minimally invasive glaucoma surgery (MIGS), cornea transplant surgery with graft rejection, graft versus host disease, dry eye disease, atopic conjunctivitis, rosacea, ocular pemphigoid, Lyell's syndrome, Steven Johnson syndrome, viral infection (e.g. HSV-1), bacterial infection, fungal infection, parasitic infection, contact lens induced neovascularization, ulceration, alkali burns, and stem cell deficiency.

In one aspect, an emulsion is provided, including a therapeutically effective amount of a multikinase inhibitor; a solubilizer; a lipophilic carrier; and one or more surfactants. In one aspect, an emulsion is provided, including a therapeutically effective amount of a multikinase inhibitor; polyoxyl oil; a solubilizer; a lipophilic carrier; and one or more surfactants.

This and other embodiments can optionally further include one or more of the following features. In some embodiments, the emulsion can be a nanoemulsion. In some embodiments, the multikinase inhibitor can be selected from afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof.

In some embodiments, the solubilizer can be a cyclic polysaccharide. In some embodiments, the cyclic polysaccharide can be selected from cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof.

In some embodiments, the lipophilic carrier can be selected from castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof. In some embodiments, the surfactant can be selected from polysorbate 20, polysorbate 40, polysorbate 60, polysorbate 80, polyoxyl-40-stearate, polyoxyl-35 castor oil, polyoxyl-40 castor oil, tocopherol and other polymeric emulsifiers and combinations thereof.

In some embodiments, the multikinase inhibitor is nintedanib, the solubilizer is 2-hydroxypropyl-beta-cyclodextrin, the lipophilic carrier is castor oil, and the surfactant is polysorbate 80, polyoxyl-35 castor oil, or a combination thereof.

In some embodiments, the multikinase inhibitor can be present in an amount of from about 0.001% w/w to about 10.0% w/w. In some embodiments, the multikinase inhibitor is nintedanib and the nintedanib can be present in an amount from about 0.01% w/w to about 10.0% w/w. In some embodiments, the multikinase inhibitor is axitinib, and the axitinib can be present in the emulsion in an amount from about 0.001% w/w to about 1.0% w/w. In some embodiments, the multikinase inhibitor is axitinib, and the axitinib can be present in the emulsion in an amount from about 0.001% w/w to about 10.0% w/w. In some embodiments, the multikinase inhibitor is pazopanib, and the pazopanib can be present in an amount from about 0.01% w/w to about 10.0% w/w. In some embodiments, the lipophilic carrier can be present in an amount from about 0.01% w/w to about 5.0% w/w.

In some embodiments, the surfactant can be present in an amount from about 0.01% w/w to about 10% w/w. In some embodiments, the solubilizer can be present in the emulsion in an amount from about 1% w/w to about 20% w/w.

In some embodiments, the emulsion can further comprise an additional constituent selected from the group consisting of a thickener, a buffering agent, a tonicity agent, an antioxidant, a preservative, and combinations thereof. In some embodiments, the thickener can be selected from the group consisting of carbomer, sodium carboxymethyl cellulose, methyl cellulose, hydroxypropyl methyl cellulose, polyvinyl alcohol, xanthan gum, and combinations thereof. In some embodiments, the thickener can be hydroxypropyl methylcellulose or sodium carboxymethylcellulose, and the thickener is present in an amount from about 0.01% w/w to about 1.0% w/w. In some embodiments, the buffering agent can be selected from the group consisting of phosphates, citrates, acetates, borates, and combinations thereof. In some embodiments, the buffering agent can be selected from the group consisting of sodium phosphate monobasic monohydrate, monosodium phosphate monohydrate, sodium phosphate dibasic heptahydrate, and boric acid, and the buffering agent is present in the emulsion in an amount sufficient to maintain the pH in the range of 4.0 to 8.0. In some embodiments, the antioxidant can be selected from the group consisting of edetate disodium, dibutylhydroxytoluene, citric acid, sodium metabisulfite, tocopherol acetate, and combinations thereof. In some embodiments, the antioxidant can be edetate disodium, and the antioxidant is present in an amount from about 0.01% w/w to about 1.0% w/w. In some embodiments, the tonicity agent can be selected from the group consisting of sodium chloride, glycerin, mannitol, potassium chloride, erythritol, and combinations thereof. In some embodiments, the tonicity agent can be glycerin, and the tonicity agent is present in an amount from about 0.1% w/w to about 10% w/w. In some embodiments, the tonicity agent can be present in an amount sufficient to maintain the osmolarity in the range of 250 to 400 mOsm/kg.

In some embodiments, the emulsion can be free of preservatives. In some embodiments, the emulsion can further comprise a preservative selected from the group consisting of BAK, PHMB, Purite®, sorbic acid, and combinations thereof.

In some embodiments, the emulsion can have an average droplet size of from about 10 nm to 100,000 nm. In some embodiments, the emulsion can have an average droplet size of 200 nm or less. In some embodiments, the emulsion can have an average droplet size of about 100 nm or less. In some embodiments, the emulsion can have an average droplet size of about 75 nm or less. In some embodiments, the emulsion can have an average droplet size of about 25 to about 200 nm (e.g., about 25 to about 150 nm, about 25 to about 100 nm, about 25 to about 75 nm, about 50 to about 200 nm, about 50 to about 150 nm, or about 50 to about 100 nm). Without being bound by any particular theory, it is believed that, at least for some emulsions (e.g., those described herein), a smaller droplet size can lead to a longer time to phase separation of an emulsion and/or a longer stability time of the emulsion. Similarly, without being bound by any particular theory, it is believed that, at least for some emulsions (e.g., those described herein), a smaller droplet size can increase the transparency of the emulsion, for example, an emulsion having a small droplet size (e.g., about 50 nm) can be almost clear, while a larger droplet size, or an emulsion that has separated, can be milky in appearance.

In some embodiments, the emulsion can remain stable for at least 6 months at 25° C. In some embodiments, the emulsion can remain stable for at least 12 months at 25° C. In some embodiments, the emulsion can remain stable for at least 24 months at 25° C. In some embodiments, the emulsion can remain stable for at least 1 month at 40° C. In some embodiments, the emulsion can remain stable for at least 2 months at 40° C.

In some embodiments, the emulsion can be formulated as an eyedrop, a cream, a gel, and ointment, a film, or a sustained release implant. In another aspect, a method is provided for prolonging the residence time of a multikinase inhibitor in the ocular surface comprising administering the any one or more of the emulsions described herein to an eye of a subject. In some embodiments, the administering can comprise applying the emulsion to the eye at least once per day. In some embodiments, the administering can comprise applying the emulsion to the eye at least twice per day. In some embodiments, the administering can comprise applying the emulsion to the eye at least three times per day.

In another aspect, a method is provided for treating an ocular condition, comprising administering any one or more of the emulsions described herein to an eye of a subject. In some embodiments, the ocular condition can be associated with angiogenesis. In some embodiments, the ocular condition can be selected from hyperemia, neovascularization, pterygium, pinguecula, glaucoma filtration surgery and minimally invasive glaucoma surgery (MIGS), cornea transplant surgery with graft rejection, graft versus host disease, dry eye disease, atopic conjunctivitis, rosacea, ocular pemphigoid, Lyell's syndrome, Steven Johnson syndrome, viral infection (e.g. HSV-1), bacterial infection, fungal infection, parasitic infection, contact lens induced neovascularization, ulceration, alkali burns, and stem cell deficiency.

In another aspect, provided herein is an emulsion comprising a therapeutically effective amount of a multikinase inhibitor, a polyoxyl oil, a lipophilic carrier, and water.

Implementations can include one or more of the following features. The emulsion can be a nanoemulsion. The multikinase inhibitor can be selected from afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof. The multikinase inhibitor can be selected from axitinib, nintedanib, and pazopanib. The multikinase inhibitor can be axitinib. The multikinase inhibitor can be nintedanib. The multikinase inhibitor can be pazopanib. The emulsion can further include a solubilizer. The solubilizer can be a cyclic polysaccharide. The cyclic polysaccharide can be selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof. The polyoxyl oil can be a polyoxyl castor oil. The polyoxyl castor oil can be polyoxyl-40 castor oil, polyoxyl-35 castor oil, or a combination thereof. The lipophilic carrier can be selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof. The emulsion can further include a surfactant selected from the group consisting of polysorbate 20, polysorbate 40, polysorbate 60, polysorbate 80, polyoxyl-40-stearate, tocopherol, and combinations thereof. The multikinase inhibitor can be nintedanib, the solubilizer can be 2-hydroxypropyl-beta-cyclodextrin, the lipophilic carrier can be castor oil, and the polyoxyl oil can be polyoxyl-35 castor oil, or a combination thereof. The multikinase inhibitor can be present in an amount from about 0.001% w/w to about 10.0% w/w. The multikinase inhibitor can be present in an amount of about 0.01% to about 1% w/w. The multikinase inhibitor can be present in an amount of about 0.1% to about 0.5% w/w. The multikinase inhibitor can be nintedanib and the nintedanib can be present in an amount from about 0.01% w/w to about 10.0% w/w. The nintedanib can be present in an amount from about 0.01% to about 1% w/w. The nintedanib can be present in an amount from about 0.1% to about 0.5% w/w. The multikinase inhibitor can be axitinib, and the axitinib can be present in the emulsion in an amount from about 0.001% w/w to about 10.0% w/w. The axitinib can be present in an amount from about 0.01% to about 1% w/w. The axitinib can be present in an amount from about 0.1% to about 0.5% w/w. The axitinib can be present in an amount from about 0.05% to about 0.5% w/w. The multikinase inhibitor can be pazopanib, and the pazopanib can be present in an amount from about 0.01% w/w to about 10.0% w/w. The pazopanib can be present in an amount from about 0.01% to about 1% w/w. The pazopanib can be present in an amount from about 0.1% to about 0.5% w/w. The lipophilic carrier can be present in an amount from about 0.01% w/w to about 5.0% w/w. The lipophilic carrier can be present in an amount from about 0.05% to about 1% w/w. The lipophilic carrier can be present in an amount from about 0.1% to about 0.5% w/w. The polyoxyl oil can be present in an amount from about 0.01% w/w to about 10% w/w. The polyoxyl oil can be present in an amount from about 0.05% to about 1% w/w. The polyoxyl oil can be present in an amount from about 0.1% to about 0.5% w/w. The emulsion can further include a solubilizer, wherein the solubilizer can be present in the emulsion in an amount from about 1% w/w to about 20% w/w. The solubilizer can be present in an amount from about 5% to about 15% w/w. The solubilizer can be present in an amount from about 8% to about 12% w/w. The emulsion can further include an additional constituent selected from the group consisting of a thickener, a buffering agent, a tonicity agent, an antioxidant, and combinations thereof. The thickener can be selected from the group consisting of carbomer, sodium carboxymethyl cellulose, methyl cellulose, hydroxypropyl methyl cellulose, polyvinyl alcohol, xanthan gum, and combinations thereof. The thickener can be hydroxypropyl methylcellulose, sodium carboxymethylcellulose, or a combination thereof. The thickener can be present in an amount from about 0.01% w/w to about 1.0% w/w. The thickener can be present in an amount from about 0.05% w/w to about 0.5% w/w. The buffering agent can be selected from the group consisting of phosphates, citrates, acetates, borates, and combinations thereof. The buffering agent can be selected from the group consisting of sodium citrate dihydrate, sodium citrate, sodium phosphate monobasic monohydrate, monosodium phosphate monohydrate, sodium phosphate dibasic heptahydrate, boric acid, and combinations thereof. The buffering agent can be selected from the group consisting of sodium citrate dihyrdrate, sodium citrate, or a combination thereof. The buffering agent can be present in the emulsion in an amount sufficient to maintain the pH in the range of 4.0 to 8.0. The buffering agent can be present in the emulsion in an amount sufficient to maintain the pH in the range of about 5.5 to about 6.5. The buffering agent can be present in an amount of about 0.01% w/w to about 1.0% w/w. The buffering agent can be present in an amount of about 0.03% w/w to about 0.06% w/w. The antioxidant can be selected from the group consisting of edetate disodium, dibutylhydroxytoluene, citric acid, sodium metabisulfite, tocopherol acetate, and combinations thereof. The antioxidant can be selected from the group consisting of edetate disodium, citric acid, and combinations thereof. The antioxidant can be present in an amount from about 0.01% to about 1.0% w/w. The antioxidant can be present in an amount from about 0.05% to about 0.5% w/w. The antioxidant can include edetate disodium, and the edetate disodium can be present in an amount from about 0.01% w/w to about 1.0% w/w. The antioxidant can include edetate disodium, and the edetate disodium can be present in an amount from about 0.05% w/w to about 0.5% w/w. The antioxidant can include citric acid, and the citric acid can be present in an amount from about 0.001% to about 0.1% w/w. The antioxidant can include citric acid, and the citric acid can be present in an amount from about 0.005% to about 0.05% w/w. The tonicity agent can be selected from the group consisting of sodium chloride, glycerin, mannitol, potassium chloride, erythritol, and combinations thereof. The tonicity agent can be glycerin. The tonicity agent can be present in an amount from about 0.1% w/w to about 10% w/w. The tonicity agent can be present in an amount from about 0.01% w/w to about 1% w/w. The tonicity agent can be present in an amount from about 0.05% w/w to about 0.5% w/w. The tonicity agent can be present in an amount sufficient to maintain the osmolarity in the range of 250 to 400 mOsm/kg. The emulsion can further include a preservative. The preservative can be selected from the group consisting of benzalkonium chloride (BAK), polyhexamethylene biguanidebiguanidide (PHMB), a stabilized oxychloro complex, sorbic acid, and combinations thereof. The emulsion can be free of preservatives. The emulsion has an average droplet size of from about 10 nm to 100,000 nm. The emulsion has an average droplet size of 200 nm or less. The emulsion can remain stable for at least 6 months at 25° C. The emulsion can remain stable for at least 12 months at 25° C. The emulsion can remain stable for at least 24 months at 25° C. The emulsion can remain stable for at least 6 months at 40° C. The emulsion can remain stable for at least 12 months at 40° C. The emulsion can remain stable for at least 24 months at 40° C. The emulsion can remain stable for at least 6 months at 50° C. The emulsion can remain stable for at least 12 months at 50° C. The emulsion can remain stable for at least 24 months at 50° C. The emulsion can remain stable for at least 6 months at 60° C. The emulsion can remain stable for at least 12 months at 60° C. The emulsion can remain stable for at least 24 months at 60° C. The emulsion can be formulated as an eyedrop, a cream, a gel, and ointment, a film.

In another aspect, provided herein is an emulsion including about 0.05% to about 1% w/w of a multikinase inhibitor, about 0.1% to about 1% w/w of a poloxyl oil, about 0.05% to about 1% w/w of a lipophilic carrier, about 5% to about 15% w/w of a solubilizer, and water.

In another aspect, provided herein is an emulsion including about 0.005% to about 2% w/w of a multikinase inhibitor, about 0.1% to about 1% w/w of a poloxyl oil, about 0.05% to about 1% w/w of a lipophilic carrier, about 5% to about 15% w/w of a solubilizer, and water.

Implementations can include one or more of the following features. The multikinase inhibitor can be present in an amount from about 0.1% to about 0.5% w/w. The polyoxyl oil can be present in an amount from about 0.3% to about 0.7% w/w. The lipophilic carrier can be present in an amount from about 0.1% to about 0.5% w/w. The solubilizer can be present in an amount from about 8% to about 12% w/w.

In another aspect, provided herein is an emulsion including about 0.1% to about 0.5% w/w of a multikinase inhibitor, about 0.3% to about 0.7% w/w of a polyoxyl oil, about 0.1% to about 0.5% w/w of a lipophilic carrier, about 8% to about 12% w/w of a solubilizer, and water.

Implementations of emulsions provided herein can include one or more of the following features. The multikinase inhibitor can be present in an amount of about 0.2% w/w. The polyoxyl oil can be present in an amount of about 0.5% w/w. The lipophilic carrier can be present in an amount of about 0.25% w/w. The solubilizer can be present in an amount of about 10% w/w.

In another aspect, provided herein is an emulsion including about 0.2% w/w of a multikinase inhibitor, about 0.5% w/w of a polyoxyl oil, about 0.25% w/w of a lipophilic carrier, about 10% w/w of a solubilizer, water.

Implementations of emulsions provided herein can include one or more of the following features. The multikinase inhibitor can be selected from the group consisting of afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof. The multikinase inhibitor can be selected from axitinib, nintedanib, and pazopanib. The multikinase inhibitor can be axitinib. The multikinase inhibitor can be nintedanib. The multikinase inhibitor can be pazopanib. The solubilizer can be a cyclic polysaccharide. The cyclic polysaccharide can be selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof. The solubilizer can include (or can be) 2-hydroxypropyl-beta-cyclodextrin. The polyoxyl oil can be a polyoxyl castor oil. The polyoxyl castor oil can be polyoxyl-40 castor oil, polyoxyl-35 castor oil, or a combination thereof. The lipophilic carrier can be selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof. The lipophilic carrier can include (or can be) castor oil. The emulsion can further include a surfactant. In some embodiments, the surfactant can be selected from the group consisting of polysorbate 20, polysorbate 40, polysorbate 60, polysorbate 80, polyoxyl-40-stearate, tocopherol, and combinations thereof. The surfactant can be present in an amount from about 0.05% to about 5% w/w. The surfactant can be present in an amount from about 0.1% to about 1% w/w. The surfactant can be present in an amount of about 0.5% w/w. The emulsion can further include an additional constituent selected from the group consisting of a thickener, a buffering agent, a tonicity agent, an antioxidant, and combinations thereof. The thickener can include hydroxypropyl methylcellulose, sodium carboxymethylcellulose, or a combination thereof. The thickener can be present in an amount from about 0.01% w/w to about 1.0% w/w. The thickener can be present in an amount from about 0.05% w/w to about 0.5% w/w. The thickener can be present in an amount of about 0.1% w/w. The buffering agent can include (or can be) sodium citrate. The buffering agent can be present in the emulsion in an amount sufficient to maintain the pH in the range of about 5.5 to about 6.5. The buffering agent can be present in an amount from about 0.01% w/w to about 1.0% w/w. The buffering agent can be present in an amount from about 0.03% w/w to about 0.06% w/w. The buffering agent can be present in an amount of about 0.045% w/w. The antioxidant can include edetate disodium, citric acid, or a combination thereof. The antioxidant can include edetate disodium, and the edetate disodium can be present in an amount from about 0.01% w/w to about 1.0% w/w. The antioxidant can include edetate disodium, and the edetate disodium can be present in an amount from about 0.05% w/w to about 0.5% w/w. The antioxidant can include edetate disodium, and the edetate disodium can be present in an amount of about 0.1% w/w. The antioxidant can include citric acid, and the citric acid can be present in an amount from about 0.001% to about 0.1% w/w. The antioxidant can include citric acid, and the citric acid can be present in an amount from about 0.005% to about 0.05% w/w. The antioxidant can include citric acid, and the citric acid can be present in an amount of about 0.015%. The tonicity agent can include (or can be) glycerin. The tonicity agent can be present in an amount from about 0.01% w/w to about 1% w/w. The tonicity agent can be present in an amount from about 0.05% w/w to about 0.5% w/w. The tonicity agent can be present in an amount of about 0.1% w/w.

In another aspect, provided herein is an emulsion including about 0.2% w/w of a multikinase inhibitor selected from the group consisting of nintedanib, axitinib, and pazopanib, about 0.5% w/w of a polyoxyl castor oil, about 0.25% w/w of castor oil, about 10% w/w of 2-hydroxypropyl-beta-cyclodextrin, and water.

Implementations can include one or more of the following features. The multikinase inhibitor can be axitinib. The multikinase inhibitor can be nintedanib. The multikinase inhibitor can be pazopanib. The polyoxyl castor oil can be polyoxyl-40 castor oil, polyoxyl-35 castor oil, or a combination thereof. The emulsion can further include polysorbate 80 in an amount of about 0.5% w/w. The emulsion can further include hydroxypropyl methylcellulose in an amount of about 0.1% w/w. The emulsion can further include sodium citrate in an amount of about 0.045% w/w. The emulsion can further include edetate disodium in an amount of about 0.1% w/w. The emulsion can further include citric acid in an amount of about 0.015%. The emulsion can further include glycerin in an amount of about 0.1% w/w.

In another aspect, provided herein is a method of prolonging the residence time of a multikinase inhibitor in the ocular surface including administering any one or more of the emulsions provided herein.

Implementations can include one or more of the following features. Administering can include applying the emulsion to the eye at least once per day. Administering can include applying the emulsion to the eye at least twice per day. Administering can include applying the emulsion to the eye at least three times per day. Administering can include applying the emulsion to the eye once per day. Administering can include applying the emulsion to the eye twice per day. Administering can include applying the emulsion to the eye three times per day.

In another aspect, provided herein is a method of treating an ocular condition, including administering any one or more of the emulsions provided herein to an eye of a subject. The ocular condition can be associated with angiogenesis.

Implementations can include one or more of the following features. The ocular condition can be selected from the group consisting of hyperemia, neovascularization, pterygium, pinguecula, glaucoma filtration surgery and minimally invasive glaucoma surgery (MIGS), cornea transplant surgery with graft rejection, graft versus host disease, dry eye disease, atopic conjunctivitis, rosacea, ocular pemphigoid, Lyell's syndrome, Steven Johnson syndrome, viral infection (e.g. HSV-1), bacterial infection, fungal infection, parasitic infection, contact lens induced neovascularization, ulceration, alkali burns, and stem cell deficiency. The emulsion can remain stable for at least 1 month at 40° C. The emulsion can remain stable for at least 6 months at 40° C. The emulsion can remain stable for at least 12 months at 40° C. The emulsion can remain stable for at least 24 months at 40° C. Administering can include applying the emulsion to the eye at least once per day. Administering can include applying the emulsion to the eye at least twice per day. Administering can include applying the emulsion to the eye at least three times per day. Administering can include applying the emulsion to the eye once per day. Administering can include applying the emulsion to the eye twice per day. Administering can include applying the emulsion to the eye three times per day.

In another aspect, provided herein is a method of preparing any of the emulsions described herein, the method including forming a primary emulsion, reducing the droplet size of the primary emulsion to form a nanoemulsion, dissolving a multikinase inhibitor into a solution, combining the nanoemulsion and solution to form a nanoemulsion including the multikinase inhibitor; and optionally, filtering the nanoemulsion including the multikinase inhibitor.

In another aspect, provided herein is a method of preparing an emulsion, the method including forming a primary emulsion, reducing the droplet size of the primary emulsion to form a nanoemulsion, dissolving a multikinase inhibitor into a solution, combining the nanoemulsion and solution to form a nanoemulsion including the multikinase inhibitor, and optionally, filtering the nanoemulsion including the multikinase inhibitor.

Implementations of the methods can include one or more of the following features. Forming the primary emulsion can include high shear mixing. Reducing the droplet size can comprise using a microfluidizer. Filtering can include using a 0.2-micron filter. The method can further include filling the filtered nanoemulsion into sterile eye dropper bottles. The sterile eye dropper bottles are multidose preservative free (MDPF) containers or low density polyethylene (LDPE) unit dose containers. The primary emulsion can include a polyoxyl oil, a lipophilic carrier, and water. The multikinase inhibitor can be selected from afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof. The multikinase inhibitor can be selected from axitinib, nintedanib, and pazopanib. The multikinase inhibitor can be axitinib. The multikinase inhibitor can be nintedanib. The multikinase inhibitor can be pazopanib. The solution can further include a solubilizer. The solubilizer can be a cyclic polysaccharide. The cyclic polysaccharide can be selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof. The polyoxyl oil can be a polyoxyl castor oil. The polyoxyl castor oil can be polyoxyl-40 castor oil, polyoxyl-35 castor oil, or a combination thereof. The lipophilic carrier can be selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof. The primary emulsion can further include a surfactant selected from the group consisting of polysorbate 20, polysorbate 40, polysorbate 60, polysorbate 80, polyoxyl-40-stearate, tocopherol, and combinations thereof. The multikinase inhibitor can be nintedanib, the solubilizer can be 2-hydroxypropyl-beta-cyclodextrin, the lipophilic carrier can be castor oil, and the polyoxyl oil can be polyoxyl-35 castor oil, or a combination thereof. The multikinase inhibitor can be present in the primary emulsion an amount from about 0.001% w/w to about 10.0% w/w. The multikinase inhibitor can be present in the primary emulsion an amount of about 0.01% to about 1% w/w. The multikinase inhibitor can be present in the primary emulsion an amount of about 0.1% to about 0.5% w/w. The lipophilic carrier can be present in the primary emulsion an amount from about 0.01% w/w to about 5.0% w/w. The lipophilic carrier can be present in the primary emulsion in an amount from about 0.05% to about 1% w/w. The lipophilic carrier can be present in the primary emulsion in an amount from about 0.1% to about 0.5% w/w. The polyoxyl oil can be present in the primary emulsion in an amount from about 0.01% w/w to about 10% w/w. The polyoxyl oil can be present in the primary emulsion an amount from about 0.05% to about 1% w/w. The polyoxyl oil can be present in the primary emulsion an amount from about 0.1% to about 0.5% w/w. The primary emulsion can further include a solubilizer, wherein the solubilizer can be present in the primary emulsion in an amount from about 1% w/w to about 20% w/w. The solubilizer can be present in the primary emulsion in an amount from about 5% to about 15% w/w. The solubilizer can be present in the primary emulsion in an amount from about 8% to about 12% w/w. The primary emulsion can further include an additional constituent selected from the group consisting of a thickener, a buffering agent, a tonicity agent, an antioxidant, and combinations thereof. The emulsion can be any of the emulsions described herein.

The details of one or more embodiments of the invention are set forth in the accompanying drawings and the description below. Other features, objects, and advantages of the invention will be apparent from the description and drawings, and from the claims.

DETAILED DESCRIPTION

The description herein sets forth details to provide an understanding of various embodiments of the invention and is made with the understanding that the provided disclosures are an exemplification of the claimed subject matter without intending to limit the claims to specific embodiments.

Accordingly, specific embodiments disclosed herein may be combined with other specific embodiments disclosed herein, including specific embodiments under various headings, which are provided for convenience and organization, but are not to be construed to limit the claims in any way.

All published documents cited herein are hereby incorporated by reference in their entirety.

As used herein, the singular forms "a", "an" and "the" are intended to include the plural forms as well, unless the context clearly indicates otherwise.

As used herein, and unless otherwise specified, the term "about", when used in connection with a numeric value or range of values which is provided to describe that the value or range of values may deviate to an extent deemed reasonable to one of ordinary skill in the art (e.g., a specific temperature or temperature range). For example, the term "about", when used in this context, can, in some embodiments, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values may vary by 5%.

Figure 1:
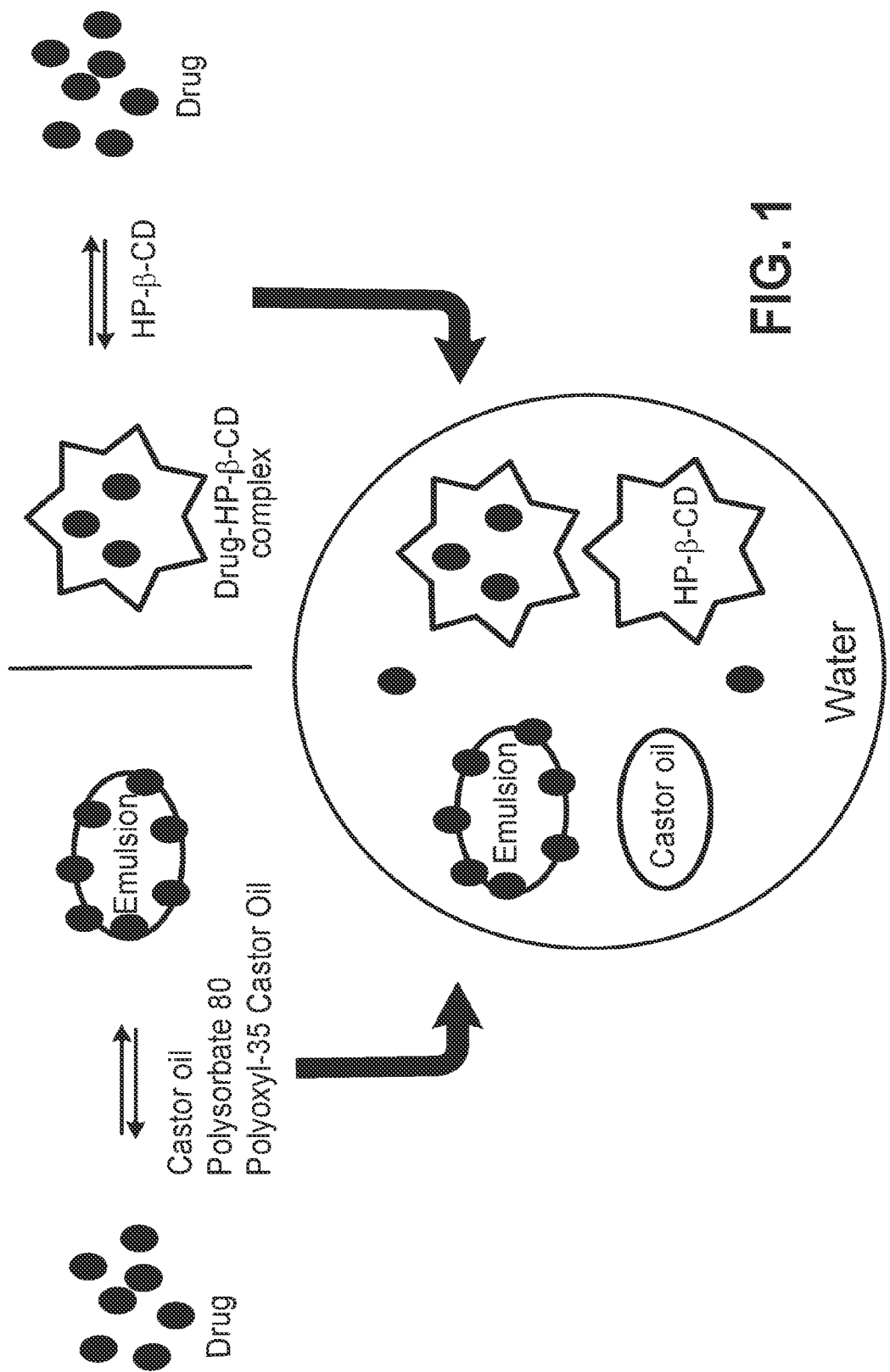
FIG. 1 is an exemplary diagram of the concept of an exemplary dual synergistic emulsion and solubilizer system utilized in some embodiments of the compositions described herein.

Nintedanib, axitinib, and pazopanib are three potent multi-kinase inhibitors against vascular endothelial growth factor receptor (VEGFR), platelet-derived growth factor receptor (PDGFR) and/or fibroblast growth factor receptor (FGFR). When formulated as an oral capsule or tablet, nintedanib, axitinib, and pazopanib are effective drug therapies to treat various types of cancers. However, nintedanib, axitinib, and pazopanib are insoluble in water with solubility at room temperature less than 0.001 mg/mL. These physical and chemical properties may limit their application and may not allow effective delivery at therapeutically effective concentrations via topical ocular administration to the target ocular tissues. Surprisingly, it has been found that a synergistic effect of an emulsion system, optionally combined with a solubilizer such as a cyclic oligosaccharide, (e.g. 2-hydroxypropyl-beta-cyclodextrin), allows successful formulation of multikinase inhibitors such as nintedanib, axitinib or pazopanib at a therapeutically effective concentration with sufficient stability to achieve desirable shelf life. For example, it has unexpectedly been found that the emulsion and, optionally, the solubilizer, lead to a greater than additive effect on the solubility of the multikinase inhibitors, such as nintedanib, axitinib or pazopanib. As shown in FIG. 1, a multikinase inhibitor such as nintedanib, axitinib or pazopanib could be dissolved into this cyclic oligosaccharide system by being effectively trapped into the central cavity of a cyclic oligosaccharide. Although a cyclic oligosaccharide, such as 2-hydroxypropyl-beta-cyclodextrin, alone can dissolve a multikinase inhibitor such as nintedanib, axitinib or pazopanib to a desired concentration, the cyclic oligosaccharide-multikinase inhibitor complex may still dissociate and cause precipitation of the multikinase inhibitor upon long term storage. Further, it has been surprisingly been shown that emulsion systems described herein can be dosed less frequently (e.g., twice a day) yet demonstrate similar or superior effectiveness and/or pharmacokinetic properties (e.g., in various tissues) compared to, for example, a solution formulation (dosed, e.g., three times a day or more).

To further improve stability, in some embodiments, a multikinase inhibitor such as nintedanib, axitinib or pazopanib, can form a complex with a lipophilic carrier system, such as a castor oil lipophilic carrier, and one or more surfactants such as polysorbate 80 and polyoxyl-35 castor oil, wherein the multikinase inhibitor would effectively dissolve into the interface of oil droplets of the lipophilic carrier system to form a stable formulation. In some embodiments, the solubility and the stability of the multikinase inhibitor formulation can be further significantly improved when the oil droplet size is less than or equal to about 200 nm. However, the concentrations of surfactant in a lipophilic carrier system alone, such as castor oil with a surfactant such as polysorbate 80 and/or polyoxyl-35 castor oil, necessary to dissolve nintedanib, axitinib or pazopanib to a desired concentration for topical ocular administration may cause irritation to the human eyes. Utilizing the emulsion or nanoemulsion of castor oil, polysorbate 80, polyoxyl-35 castor oil at low concentrations, optionally in combination with a cyclic oligosaccharide, creates a synergistic effect and can improve the overall solubility of nintedanib, axitinib or pazopanib to achieve targeted solubility and formulation stability with sufficient shelf life.

In some embodiments, the compositions described herein can remain stable for at least 6 months, at least 8 months, at least 10 months, at least 12 months, at least 15 months, at least 18 months, at least 24 months, or more at room temperate (25° C.). In some embodiments, the compositions described herein can remain stable for at least 1 month, 2 months, 3 months, 4 months, 5 months, or 6 months or more at elevated temperatures (e.g., 40° C. to 60° C.). In some embodiments, the compositions described herein can remain stable for at least 1 month, 2 months, 3 months, 4 months, 5 months, or 6 months or more at 40° C. In some embodiments, the compositions described herein can remain stable for at least 1 month, 2 months, 3 months, 4 months, 5 months, or 6 months or more at 60° C.

Stability can be determined by methods known in the art, including, e.g., observing formula appearance, monitoring for precipitation, monitoring pH changes, monitoring changes in osmolarity, monitoring emulsion phase stability, monitoring emulsion droplet size, and the like. In some embodiments, the compositions maintain a pH range of from about pH 4 to about pH 8 for at least 6 months, at least 8 months, at least 10 months, at least 12 months, at least 15 months, at least 18 months, at least 24 months, or more at room temperate (25° C.). In some embodiments, the compositions maintain a pH range of from about pH 4 to about pH 8 for at least 1 month, 2 months, 3 months, 4 months, 5 months, or 6 months or more at elevated temperatures (e.g., 40° C. to 60° C.). In some embodiments, the compositions maintain a pH range of from about pH 5 to about pH 6 for at least 6 months, at least 8 months, at least 10 months, at least 12 months, at least 15 months, at least 18 months, at least 24 months, or more at room temperate (25° C.). In some embodiments, the compositions maintain a pH range of from about pH 5 to about pH 6 for at least 1 month, 2 months, 3 months, 4 months, 5 months, or 6 months or more at elevated temperatures (e.g., 40° C. to 60° C.). In some embodiments, the multikinase inhibitor does not precipitate out of the compositions for at least 6 months, at least 8 months, at least 10 months, at least 12 months, at least 15 months, at least 18 months, at least 24 months, or more at room temperate (25° C.). In some embodiments, the multikinase inhibitor does not precipitate out of the compositions for at least 1 month, 2 months, 3 months, 4 months, 5 months, or 6 months or more at elevated temperatures (e.g., 40° C. to 60° C.).

In some embodiments, the compositions maintain an osmolarity of from about 250 mOsm/kg to about 400 mOsm/kg for at least 6 months, at least 8 months, at least 10 months, at least 12 months, at least 15 months, at least 18 months, at least 24 months, or more at room temperate (25° C.). In some embodiments, the compositions maintain an osmolarity of from about 250 mOsm/kg to about 400 mOsm/kg for at least 1 month, 2 months, 3 months, 4 months, 5 months, or 6 months or more at elevated temperatures (e.g., 40° C. to 60° C.).

In some embodiments, at least 99% of the multikinase inhibitor remains dissolved in the composition for at least 6 months, at least 8 months, at least 10 months, at least 12 months, at least 15 months, at least 18 months, at least 24 months, or more at room temperate (25° C.). In some embodiments, at least 99% of the multikinase inhibitor remains dissolved in the composition for at least 1 month, 2 months, 3 months, 4 months, 5 months, or 6 months or more at elevated temperatures (e.g., 40° C. to 60° C.). In some embodiments, at least 99.5% of the multikinase inhibitor remains dissolved in the composition for at least 6 months, at least 8 months, at least 10 months, at least 12 months, at least 15 months, at least 18 months, at least 24 months, or more at room temperate (25° C.). In some embodiments, at least 99.5% of the multikinase inhibitor remains dissolved in the composition for at least 1 month, 2 months, 3 months, 4 months, 5 months, or 6 months or more at elevated temperatures (e.g., 40° C. to 60° C.).

In some embodiments, 100% of the multikinase inhibitor remains dissolved in the composition for at least 6 months, at least 8 months, at least 10 months, at least 12 months, at least 15 months, at least 18 months, at least 24 months, or more at room temperate (25° C.). In some embodiments, 100% of the multikinase inhibitor remains dissolved in the composition for at least 1 month, 2 months, 3 months, 4 months, 5 months, or 6 months or more at elevated temperatures (e.g., 40° C. to 60° C.).

This unique formulation system is also well tolerated in humans and animals and could be an effective treatment option for various ocular conditions, such as diseases affecting the anterior segment of the eye. Furthermore, an emulsion, such as a nanoemulsion, with the addition of thickening agents, such as sodium carboxymethylcellulose or hydroxypropyl methylcellulose, may increase drug half-life on the affected ocular surface when administered topically, resulting in an increase in drug residence time at ocular surface and a decrease in dosing frequency while still maintaining pharmaceutically effective treatment.

In some embodiments, the disclosure provides an ophthalmic composition comprising a therapeutically effective amount of a multikinase inhibitor (e.g., nintedanib or axitinib or pazopanib), optionally wherein said combination of an emulsion, such as a nanoemulsion, with a cyclic oligosaccharide, such as 2-hydroxypropyl-beta-cyclodextrin, as a solubilizer, is suitable for topical administration to an eye. In some embodiments, a method is provided for treating an ocular condition associated with angiogenesis, such as hyperemia, neovascularization, pterygium, pinguecula, glaucoma filtration surgery and minimally invasive glaucoma surgery (MIGS), cornea transplant surgery with graft rejection, graft versus host disease, dry eye disease, atopic conjunctivitis, rosacea, ocular pemphigoid, Lyell's syndrome, Steven Johnson syndrome, viral infection (e.g. HSV-1), bacterial infection, fungal infection, parasitic infection, contact lens induced neovascularization, ulceration, alkali burns, stem cell deficiency, is also disclosed herein, and wherein at least one symptom of the ocular condition is alleviated, regressed, or halted. As used herein, unless otherwise specified, the term "nintedanib or axitinib or pazopanib" include their free base, salts, analogues, esters, and combinations thereof.

Furthermore, the compositions disclosed herein could comprise compounds with a similar pharmacological profile and physical and chemical properties of multikinase inhibitors, such as afatinib, amuvatinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, palbociclib, ponatinib, quizartinib, regorafenib, ruxolitinib, sorafenib, sunitinib, tandutinib, tivantinib, tivozanib, trametinib, vandetanib, vatalanib, and vemurafenib.

In some embodiments, the compositions described herein can be useful for treating one or more ocular conditions in an affected eye of a subject. Methods are provided herein, comprising administering a composition described herein to an affected eye of a subject. In some embodiments, the ocular condition can be any condition of an eye, resulting from an angiogenesis in the anterior segment or posterior segment of an eye. The subject to be treated can be of any age, or gender. In some embodiments, the subject can be human. In some embodiments, the subject can be a non-human mammal.

In some embodiments, a pharmaceutical composition disclosed herein may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects. As used herein, a dosage is considered effective if it ameliorates, prevents, reduces, or eliminates the symptoms associated with the ocular condition to be treated.

In some embodiments, the multikinase inhibitor, such as nintedanib or axitinib or pazopanib, can be present in the ophthalmic compositions described herein in an amount from about 0.001% to about 10.0% (w/w). In some embodiments, the multikinase inhibitor is present in an amount of from about 0.005% to about 2% (w/w), from about 0.001% to about 1% (w/w), from about 0.001% to about 0.005% (w/w), from about 0.005% to about 0.01% (w/w), from about 0.01% to about 0.05% (w/w), from about 0.05% to about 0.1% (w/w), from about 0.01% to about 1% (w/w), from about 0.05% to about 0.5%, from about 0.01% to about 0.8% (w/w), from about 0.3% to about 0.7% (w/w), from about 0.4% to about 0.6% (w/w), from about 0.1% to about 10% (w/w), from about 0.1% to about 0.5% (w/w), from about 0.2% to about 8% (w/w), from about 0.4% to about 5% (w/w), or from about 0.4% to about 2% (w/w). In some embodiments the multikinase inhibitor is present at a concentration of about 0.5% (w/w). In some embodiments, the multikinase inhibitor is preset at a concentration of about 0.2% (w/w). In some embodiments, at least 99% of the multikinase inhibitor is dissolved in the composition. In some embodiments, at least 99.5% of the multikinase inhibitor is dissolved in the composition. In some embodiments, 100% of the multikinase inhibitor is dissolved in the composition.

In some embodiments, the disclosed compositions can be emulsions, solutions, suspensions, gels, ointments, occlusive films, or a sustained release formulation and they can be preserved or non-preserved formulations. In some embodiments, the disclosed compositions can be emulsions. In some embodiments, the disclosed compositions can be nanoemulsions. An emulsion can have any appropriate droplet size (e.g., about 10 nm to about 10,000 nm, about 100 nm to about 500 nm, less than about 500 nm, less than about 400 nm, less than about 300 nm, less than about 200 nm, or less than about 100 nm). The compositions can be formulated as eye drops, creams, ointments, films, gels and implants (e.g., a sustained release implant) that can be applied to an eye. The formulations can be administered to an eye of a subject in need thereof.

Listed in Table 1 are non-limiting examples of possible formulation ingredients and their exemplary concentrations.

TABLE 1

| Function | Ingredient | Composition (% w/w) |
|---|---|---|
| Active | nintedanib | 0.01-10.0 |
|  | axitinib | 0.001-10.0 |
|  | pazopanib | 0.01-10.0 |
| Thickener/ Viscosity Agent | carbomer, sodium carboxymethyl cellulose, methyl cellulose, hydroxypropyl methyl cellulose, polyvinyl alcohol, Zanthan gum | 0-3.0 |
| Antioxidant Agent | edetate disodium, dibutylhydroxytoluene, citric acid, sodium metabisulfite, tocopherol acetate | 0-1.0 |
| Surfactant | polysorbate 20, polysorbate 40, polysorbate 60, polysorbate 80, polyoxyl-40-stearate, polyoxyl-35 castor oil, polyoxyl-40 castor oil, tocopherol and other polymeric emulsifiers | 0-10.0 |
| Lipophilic Vehicle | castor oil, squalene, isostearyl isostearate, isopropyl myristate, mineral oil, silicone oil, medium chain triglycerides | 0-10.0 |
| Buffering Agent | sodium citrate dihydrate, sodium citrate boric acid, monosodium phosphate monohydrate, sodium phosphate dibasic heptahydrate, sodium phosphate monobasic monohydrate | 0-2.0 |
| Tonicity Agent | glycerin, erythritol, mannitol, potassium chloride, sodium chloride | 0-3.0 |
| Solubilizer/ Solubility Enhancing Agent | cyclodextrin, alpha-cyclodextrin, beta-cyclodextrin, gamma-cyclodextrin, 2-hydroxypropyl-beta-cyclodextrin, 2-hydroxypropyl-alpha-cyclodextrin, 2-hydroxypropyl-gamma-cyclodextrin, sulfobutyl ether-beta-cyclodextrin | 0-20.0 |
| Preservative | benzalkonium chloride, Purite, sorbic acid, PHMB and other ophthalmic preservatives | 0-2.0 |
| Hydrophilic Vehicle | water | 0-99.0 |

In some embodiments, the composition can comprise a lipophilic carrier such as, castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides, and combinations thereof. In some embodiments, the lipophilic carrier can include castor oil. In some embodiments, the lipophilic vehicle can be present in an amount of from about 0% to about 10% of the composition by weight (e.g., about 0.001% to about 10% (w/w), about 0.01% to about 5.0% (w/w), about 0.05% to about 1.0% (w/w), or about 0.1% to about 0.5% (w/w)). In some embodiments, the lipophilic carrier can be present in an amount of about 0.25% (w/w).

In some embodiments, the composition can comprise one or more surfactants, such as polysorbate 20, polysorbate 40, polysorbate 60, polysorbate 80, polyoxyl-40-stearate, polyoxyl-35 castor oil, polyoxyl-40 castor oil, tocopherol, other polymeric emulsifiers, and combinations thereof. In some embodiments, the composition can include a surfactant that is a polyoxyl oil, such as a polyoxyl castor oil (e.g., polyoxyl-35 castor oil, polyoxyl-40 castor oil, or a combination thereof) (e.g., a CREMOPHOR® or a KOLLIPHOR®). In some such embodiments, the composition can further include one or more additional surfactants that are not a polyoxyl oil (e.g., a polysorbate, such as polysorbate 20, polysorbate 40, polysorbate 60, polysorbate 80, or a combination thereof). In some embodiments, a surfactant can be present in an amount of from about 0% to about 10% by weight of the composition (e.g., about 0.001% to about 10% (w/w), about 0.050% to about 50% (w/w), about 0.010% to about 1.0% (w/w), or about 0.1% to about 0.5% (w/w)). In some embodiments, a surfactant can be present in an amount of about 0.5% (w/w). In some embodiments, a polyoxyl oil can be present in an amount of from about 0% to about 10% by weight of the composition (e.g., about 0.001% to about 10% (w/w), about 0.05% to about 5% (w/w), about 0.01% to about 1.0% (w/w), or about 0.1% to about 0.5% (w/w)). In some embodiments, a polyoxyl oil can be present in an amount of about 0.5% (w/w). In some such embodiments, a second surfactant can be present in an amount of from about 0% to about 10% by weight of the composition (e.g., about 0.001% to about 10% (w/w), about 0.05% to about 5% (w/w), about 0.01% to about 1.0% (w/w), or about 0.1% to about 0.5% (w/w)). In some embodiments, a second surfactant can be present in an amount of about 0.5% (w/w).

In some embodiments, the composition can comprise a tonicity agent, such as sodium chloride, glycerin, mannitol, potassium chloride, erythritol, and combinations thereof in an amount sufficient to maintain the osmolarity in the range of 250 to 400 mOsm/kg (e.g., about 250 to about 300 mOsm/kg or about 300 to about 400 mOsm/kg). In some embodiments, a tonicity agent can include glycerin. In some embodiments, a tonicity agent can be present in an amount of from about 0 to about 10% by weight of the composition (e.g., about 0% to about 3%, about 0.1% to about 10% (w/w), about 0.01% to about 1% (w/w), or about 0.05% to about 0.5% (w/w)). In some embodiments, a tonicity agent can be present in an amount of about 0.1% (w/w).

In some embodiments, the composition can comprise an antioxidant, such as edetate disodium, dibutylhydroxytoluene, citric acid, sodium metabisulfite, tocopherol acetate, and combinations thereof. In some embodiments, an antioxidant can be selected from the group consisting of edetate disodium, citric acid, and combinations thereof. In some embodiments, the antioxidant can be present in an amount of from about 0 to about 1% by weight of the composition (e.g., about 0.01% to about 1.0% (w/w) or about 0.05% to about 0.5% (w/w). In some embodiments, the antioxidant can be present in an amount of about 0.115% (w/w). In some embodiments, the antioxidant can comprise edetate disodium, and the edetate disodium can be present in an amount of about 0.01% to about 1.0% (w/w), about 0.05% to about 0.5% (w/w), or about 0.1% to about 0.5% (w/w)). In some embodiments, the antioxidant can comprise citric acid, and the citric acid can be present in an amount of about 0.001% to about 0.1% (w/w), 0.005% to about 0.05% (w/w), or about 0.015% (w/w).

In some embodiments, the composition can include one or more buffering agents. Suitable buffering agents include, but are not limited to, phosphates, citrates, acetates, borates, and combinations thereof. In some embodiments, the buffering agent can be selected from the group consisting of sodium citrate dihydrate, sodium citrate, sodium phosphate monobasic monohydrate, monosodium phosphate monohydrate, sodium phosphate dibasic heptahydrate, boric acid, and combinations thereof. In some embodiments, the buffering agent can be selected from the group consisting of sodium citrate dihyrdrate, sodium citrate, and a combination thereof. In some embodiments, the buffering agent can be selected from the group consisting of sodium citrate dihyrdrate, sodium citrate, or a combination thereof. The amount of buffer component employed is sufficient to maintain the pH of the composition in a range of about 4 to about 8 (e.g., about 5.0 to about 7.0, or about 5.5 to about 6.5) throughout product shelf life. In certain embodiments, the buffer is present in an amount of about 0 to about 2.0% by weight of the composition (e.g., about 0.01% to about 1.0% (w/w) or about 0.03% to about 0.06% (w/w)). In some embodiments, the buffer is present in an amount of about 0.045% (w/w).

In some embodiments, the composition can include a thickener or viscosity agent. In some embodiments, the viscosity agent can be selected from carbomer, sodium carboxymethyl cellulose, methyl cellulose, hydroxypropyl methyl cellulose (e.g., a HPMC with an average content of methoxyl group of about 29% and an average content of hydroxypropyl group of about 10%), polyvinyl alcohol, xanthan gum, and combinations thereof. In some embodiments, the thickener can be hydroxypropyl methylcellulose, sodium carboxymethylcellulose, or a combination thereof. In some embodiments, the viscosity agent can be present in an amount of about 0% to about 3% by weight of the composition (e.g., about 0.01% to about 1.0% (w/w) or about 0.05% to about 0.5% (w/w)). In some embodiments, the thickener can be present in an amount of about 0.1% (w/w).

In some embodiments, the composition can include a solubilizer or solubility enhancing agent. In some embodiments, the solubilizer can be a cyclic oligosaccharide. In some embodiments, the solubilizer or solubility enhancing agent can be selected from cyclodextrin, alpha-cyclodextrin, beta-cyclodextrin, gamma-cyclodextrin, 2-hydroxypropyl-alpha-cyclodextrin, 2-hydroxypropyl-beta-cyclodextrin (sometimes also called HPBCD or HP-beta-CD), 2-hydroxypropyl-gamma-cyclodextrin, sulfobutyl ether-beta-cyclodextrin and combinations thereof. In some embodiments, the solubilizer can include 2-hydroxypropl-beta-cyclodextrin. In some embodiments, the solubilizer or solubility enhancing agent can be present in an amount of about 0% to about 20% by weight of the composition (e.g., about 1% to about 20% (w/w), about 5% to about 15% (w/w), or about 8% to about 12% (w/w). In some embodiments, the solubilizer or solubility enhancing agent can be present in an amount of about 10% (w/w).

In some embodiments, the composition can be administered topically in the form of an eye drop, cream, ointment, film, suspension, gel or the like. In some embodiments, the composition can be administered to a single eye or to both eyes of a subject.

The compositions of or used in, the present disclosure may include one or more other components in amounts effective to provide one or more useful properties and/or benefits. For example, although the present compositions may be substantially free of added preservative components, in other embodiments, the present compositions include effective amounts of preservative components. Examples of such preservative components include, without limitation, a stabilized oxychloro complex (e.g., PURITE®), quaternary ammonium preservatives such as benzalkonium chloride ("BAC or "BAK"), sorbic acid, and polyoxamer; biguanidebigunanide preservatives such as polyhexamethylene biguanidebiguandide (PH-MB); methyl and ethyl parabens; hexetidine; chlorite components, such as stabilized chlorine dioxide, metal chlorites and the like; other ophthalmically acceptable preservatives and mixtures thereof. The concentration of the preservative component, if any, in the present compositions is a concentration effective to preserve the composition and is often and generally used in a range of about 0% to about 2.0% by volume of the composition.

Typically, water makes up the balance of compositions described herein.

In some embodiments provided herein are compositions with varying combinations of ingredients. Exemplary compositions are shown in Table A.

TABLE A

| Component | Exemplary component | Exemplary Amount A1 (w/w) | Exemplary Amount A2 (w/w) | Exemplary Amount A3 (w/w) |
|---|---|---|---|---|
| Multikinase inhibitor | Nintedanib, axitinib, or pazopanib | about 0.005%-about 2% | About 0.1%-about 0.5% | About 0.2% |
| Polyoxyl oil | Polyoxyl-35 castor oil | About 0.1%-about 1% | About 0.3%-about 0.7% | About 0.5% |
| Lipophilic carrier | Castor oil | About 0.05%-about 1% | About 0.1%-about 0.5% | About 0.25% |
| Solubilizer | 2-hydroxypropyl-beta-cyclodextrin | About 5%-about 15% | About 8%-about 12% | About 10% |

Additional components may be present in the compositions provided herein. Exemplary additional components are shown in Table B. Each combination of Table A and Table B is explicitly contemplated (e.g., A1B1, A2B1, A3B1, A1B2, A2B2, A3B2, A1B3, A2B3, and A3B3).

TABLE B

| Component | Exemplary component | Exemplary Amount B1 (w/w) | Exemplary Amount B2 (w/w) | Exemplary Amount B3 (w/w) |
|---|---|---|---|---|
| Surfactant | Polysorbate 80 | About 0.05%-about 5% | About 0.1% to about 1% | About 0.5% |
| Thickener | Hydroxypropyl methylcellulose | About 0.01%-about 1.0% | About 0.05%-about 0.5% | About 0.1% |
| Buffering Agent | Sodium citrate | About 0.01%-about 1.0% | About 0.03%-0.06% | About 0.045% |
| Antioxidant | Edetate disodium and/or citric acid | About 0.01%-about 1.0% | About 0.05%-about 0.5% | About 0.115% |
| Tonicity agent | Glycerin | About 0.01%-about 1% | About 0.05%-about 0.5% | About 0.1% |

Also provided herein are methods of preparing compositions (e.g., emulsions). In some embodiments, the compositions can be any of the compositions described herein.

In some embodiments, the methods can include dissolving a multikinase inhibitor into a primary emulsion, reducing the droplet size of the primary emulsion to form a nanoemulsion, and filtering the nanoemulsion. In some embodiments, dissolving the multikinase inhibitor can include high shear mixing. In some embodiments, the methods can include forming a primary emulsion, reducing the droplet size of the primary emulsion to form a nanoemulsion, dissolving a multikinase inhibitor into a solution, combining the nanoemulsion and solution to form a nanoemulsion comprising the multikinase inhibitor, and optionally, filtering the nanoemulsion comprising the multikinase inhibitor. In some embodiments, dissolving a multikinase inhibitor into a solution can include dissolving a multikinase inhibitor into a solution including a solubilizer (e.g., any of the solubilizers described herein). In some embodiments, the solution can further include a buffer (e.g., sodium citrate), an antioxidant (e.g., citric acid and/or trisodium EDTA), a thickener (e.g., HPMC), or a combination thereof.

In some embodiments, reducing the droplet size can include using a microfluidizer. Filtering the nanoemulsion can be performed using a filter of any appropriate size (e.g., a 0.2-miron filter). In some embodiments, the method can include filling the filtered nanoemulsion into sterile eye dropper bottles. Non-limiting examples of sterile eye dropper bottles include multidose preservative free (MDPF) containers or low density polyethylene (LDPE) unit dose containers. In some embodiments a primary emulsion can include a polyoxyl oil, a lipophilic carrier, and water. In some embodiments, a primary emulsion can further include a surfactant. In some embodiments, a primary emulsion can further include a solubilizer. In some embodiments, a primary emulsion can include one or more of a thickener, a buffering agent, a tonicity agent, an antioxidant, and combinations thereof.

The frequency, duration, and dosage of the administration are determined by the prescribing physician. The dosage can vary depending on the dosage formulation. Frequency of administration can be one or more times daily (such as once, twice, three, or four or more times daily), bi-weekly (such as every two weeks or twice a week), and/or monthly. Duration of administration can continue until the ocular condition to be treated is resolved, that is, until one or more symptoms of the ocular condition are ameliorated, reduced, or eliminated. In some embodiments, a composition described herein can be administered for hours, days, weeks, months, or years.

A symptom is considered to be alleviated or ameliorated if it is prevented, reduced or eliminated. A symptom is prevented in a patient that typically experiences a particular symptom with the ocular condition and the patient does not experience the onset of the symptom following administration of the disclosed composition. A reduction of a symptom is considered achieved if there is a 5%, 10%, 20%, 50%, 75%, 90% or more reduction in the severity or duration of one or more symptoms associated with the ocular condition in a patient. An elimination of one or more symptoms associated with the ocular condition is achieved when it ceases to be present or substantially present in a patient. In some embodiments an elimination of one or more symptoms associated with the ocular condition is achieved when 90% or more of one or more symptoms cease to be present.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The recitations of numerical ranges by endpoints include all numbers subsumed within that range (e.g., 1 to 5 includes 1, 1.5, 2, 2.75, 3, 3.80, 4, 5, etc.).

The terms "a," "an," "the" and similar referents used in the context of describing the invention are to be construed to cover both the singular and the plural, unless otherwise indicated herein or clearly contradicted by context. Recitation of ranges of values herein is merely intended to serve as a shorthand method of referring individually to each separate value falling within the range.

Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention. Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments of this invention are described herein. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention is not limited to that precisely as shown and described. Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein.

EXEMPLARY EMBODIMENTS

Embodiment 1 is an emulsion comprising:
 a therapeutically effective amount of a multikinase inhibitor;
 a polyoxyl oil;
 a lipophilic carrier;
 and
 water.

Embodiment 2 is the emulsion of embodiment 1, wherein the emulsion is a nanoemulsion.

Embodiment 3 is the emulsion of any one of embodiments 1 to 2, wherein the multikinase inhibitor is selected from afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof.

Embodiment 4 is the emulsion of embodiment 3, wherein the multikinase inhibitor is selected from axitinib, nintedanib, and pazopanib.

Embodiment 5 is the emulsion of embodiment 3, wherein the multikinase inhibitor is axitinib.

Embodiment 6 is the emulsion of embodiment 3, wherein the multikinase inhibitor is nintedanib.

Embodiment 7 is the emulsion of embodiment 3, wherein the multikinase inhibitor is pazopanib.

Embodiment 8 is the emulsion of any one of embodiments 1 to 7, further comprising a solubilizer.

Embodiment 9 is the emulsion of any one of embodiments 1 to 8, wherein the solubilizer is a cyclic polysaccharide.

Embodiment 10 is the emulsion of embodiment 4, wherein the cyclic polysaccharide is selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof.

Embodiment 11 is the emulsion of any one of embodiments 1 to 10, wherein the polyoxyl oil is a polyoxyl castor oil.

Embodiment 12 is the emulsion embodiment 11, wherein the polyoxyl castor oil is polyoxyl-40 castor oil, polyoxyl-35 castor oil, or a combination thereof.

Embodiment 13 is the emulsion of any one of embodiments 1 to 12, wherein the lipophilic carrier is selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof.

Embodiment 14 is the emulsion of any one of embodiments 1 to 13, further comprising a surfactant selected from the group consisting of polysorbate 20, polysorbate 40, polysorbate 60, polysorbate 80, polyoxyl-40-stearate, tocopherol, and combinations thereof.

Embodiment 15 is the emulsion of embodiment 1, wherein the multikinase inhibitor is nintedanib, the solubilizer is 2-hydroxypropyl-beta-cyclodextrin, the lipophilic carrier is castor oil, and the polyoxyl oil is polyoxyl-35 castor oil, or a combination thereof.

Embodiment 16 is the emulsion of any one of embodiments 1 to 15, wherein the multikinase inhibitor is present in an amount from about 0.001% w/w to about 10.0% w/w.

Embodiment 17 is the emulsion of embodiment 16, wherein the multikinase inhibitor is present in an amount of about 0.01% to about 1% w/w.

Embodiment 18 is the emulsion of embodiment 16, wherein the multikinase inhibitor is present in an amount of about 0.1% to about 0.5% w/w.

Embodiment 19 is the emulsion of any one of embodiments 1 to 14, wherein the multikinase inhibitor is nintedanib and the nintedanib is present in an amount from about 0.01% w/w to about 10.0% w/w.

Embodiment 20 is the emulsion of embodiment 19, wherein the nintedanib is present in an amount from about 0.01% to about 1% w/w.

Embodiment 21 is the emulsion of embodiment 19, wherein the nintedanib is present in an amount from about 0.1% to about 0.5% w/w.

Embodiment 22 is the emulsion of any one of embodiments 1 to 14, wherein the multikinase inhibitor is axitinib, and the axitinib is present in the emulsion in an amount from about 0.001% w/w to about 10.0% w/w.

Embodiment 23 is the emulsion of embodiment 22, wherein the axitinib is present in an amount from about 0.01% to about 1% w/w.

Embodiment 24 is the emulsion of embodiment 22, wherein the axitinib is present in an amount from about 0.05% to about 0.5% w/w.

Embodiment 25 is the emulsion of any one of embodiments 1 to 14, wherein the multikinase inhibitor is pazopanib, and the pazopanib is present in an amount from about 0.01% w/w to about 10.0% w/w.

Embodiment 26 is the emulsion of embodiment 25, wherein the pazopanib is present in an amount from about 0.01% to about 1% w/w.

Embodiment 27 is the emulsion of embodiment 25, wherein the pazopanib is present in an amount from about 0.1% to about 0.5% w/w.

Embodiment 28 is the emulsion of any one of embodiments 1 to 27, wherein the lipophilic carrier is present in an amount from about 0.01% w/w to about 5.0% w/w.

Embodiment 29 is the emulsion of embodiment 28, wherein the lipophilic carrier is present in an amount from about 0.05% to about 1% w/w.

Embodiment 30 is the emulsion of embodiment 28, wherein the lipophilic carrier is present in an amount from about 0.1% to about 0.5% w/w.

Embodiment 31 is the emulsion of any one of embodiments 1 to 30, wherein the polyoxyl oil is present in an amount from about 0.01% w/w to about 10% w/w.

Embodiment 32 is the emulsion of embodiment 31, wherein the polyoxyl oil is present in an amount from about 0.05% to about 1% w/w.

Embodiment 33 is the emulsion of embodiment 31, wherein the polyoxyl oil is present in an amount from about 0.1% to about 0.5% w/w.

Embodiment 34 is the emulsion of any one of embodiments 1 to 33, further comprising a solubilizer, wherein the solubilizer is present in the emulsion in an amount from about 1% w/w to about 20% w/w.

Embodiment 35 is the emulsion of embodiment 34, wherein the solubilizer is present in an amount from about 5% to about 15% w/w.

Embodiment 36 is the emulsion of embodiment 34, wherein the solubilizer is present in an amount from about 8% to about 12% w/w.

Embodiment 37 is the emulsion of any one of embodiments 1 to 36, further comprising an additional constituent selected from the group consisting of a thickener, a buffering agent, a tonicity agent, an antioxidant, and combinations thereof.

Embodiment 38 is the emulsion of embodiment 37, wherein the thickener is selected from the group consisting of carbomer, sodium carboxymethyl cellulose, methyl cellulose, hydroxypropyl methyl cellulose, polyvinyl alcohol, xanthan gum, and combinations thereof.

Embodiment 39 is the emulsion of embodiment 38, wherein the thickener is hydroxypropyl methylcellulose, sodium carboxymethylcellulose, or a combination thereof.

Embodiment 40 is the emulsion of any one of embodiments 37-39, wherein the thickener is present in an amount from about 0.01% w/w to about 1.0% w/w.

Embodiment 41 is the emulsion of any one of embodiments 37-39, wherein the thickener is present in an amount from about 0.05% w/w to about 0.5% w/w.

Embodiment 42 is the emulsion any one of embodiments 37-41, wherein the buffering agent is selected from the group consisting of phosphates, citrates, acetates, borates, and combinations thereof.

Embodiment 43 is the emulsion of any one of embodiments 37-42, wherein the buffering agent is selected from the group consisting of sodium citrate dihydrate, sodium citrate, sodium phosphate monobasic monohydrate, monosodium phosphate monohydrate, sodium phosphate dibasic heptahydrate, boric acid, and combinations thereof.

Embodiment 44 is the emulsion of any one of embodiments 37-43, wherein the buffering agent is selected from the group consisting of sodium citrate dihyrdrate, sodium citrate, or a combination thereof.

Embodiment 45 is the emulsion of any one of embodiments 37-44, wherein the buffering agent is present in the emulsion in an amount sufficient to maintain the pH in the range of 4.0 to 8.0.

Embodiment 46 is the emulsion of any one of embodiments 37-44, wherein the buffering agent is present in the emulsion in an amount sufficient to maintain the pH in the range of about 5.5 to about 6.5.

Embodiment 47 is the emulsion of any one of embodiments 37-46, wherein the buffering agent is present in an amount of about 0.01% w/w to about 1.0% w/w.

Embodiment 48 is the emulsion of any one of embodiments 37-46, wherein the buffering agent is present in an amount of about 0.03% w/w to about 0.06% w/w.

Embodiment 49 is the emulsion any one of embodiments 37-48, wherein the antioxidant is selected from the group consisting of edetate disodium, dibutylhydroxytoluene, citric acid, sodium metabisulfite, tocopherol acetate, and combinations thereof.

Embodiment 50 is the emulsion of any one of embodiments 37-48, wherein the antioxidant is selected from the group consisting of edetate disodium, citric acid, and combinations thereof.

Embodiment 51 is the emulsion of any one of embodiments 37-50, wherein the antioxidant is present in an amount from about 0.01% to about 1.0% w/w.

Embodiment 52 is the emulsion of any one of embodiments 37-50, wherein the antioxidant is present in an amount from about 0.05% to about 0.5% w/w.

Embodiment 53 is the emulsion of any one of embodiments 37-52, wherein the antioxidant comprises edetate disodium, and the edetate disodium is present in an amount from about 0.01% w/w to about 1.0% w/w.

Embodiment 54 is the emulsion of any one of embodiments 37-52, wherein the antioxidant comprises edetate disodium, and the edetate disodium is present in an amount from about 0.05% w/w to about 0.5% w/w.

Embodiment 55 is the emulsion of any one of embodiments 37-54, wherein the antioxidant comprises citric acid, and the citric acid is present in an amount from about 0.001% to about 0.1% w/w.

Embodiment 56 is the emulsion of any one of embodiments 37-54, wherein the antioxidant comprises citric acid, and the citric acid is present in an amount from about 0.005% to about 0.05% w/w.

Embodiment 57 is the emulsion of any one of embodiments 37-56, wherein the tonicity agent is selected from the group consisting of sodium chloride, glycerin, mannitol, potassium chloride, erythritol, and combinations thereof.

Embodiment 58 is the emulsion of any one of embodiments 37-56, wherein the tonicity agent is glycerin.
Embodiment 59 is the emulsion of any one of embodiments 37-58, wherein the tonicity agent is present in an amount from about 0.1% w/w to about 10% w/w.
Embodiment 60 is the emulsion of any one of embodiments 37-58, wherein the tonicity agent is present in an amount from about 0.01% w/w to about 1% w/w.
Embodiment 61 is the emulsion of any one of embodiments 37-58, wherein the tonicity agent is present in an amount from about 0.05% w/w to about 0.5% w/w.
Embodiment 62 is the emulsion of any one of embodiments 37 to 61, wherein the tonicity agent is present in an amount sufficient to maintain the osmolarity in the range of 250 to 400 mOsm/kg.
Embodiment 63 is the emulsion of any one of embodiments 1-62, wherein the emulsion further comprises a preservative.
Embodiment 64 is the emulsoion of embodiment 63, wherein the preservative is selected from the group consisting of benzalkonium chloride (BAK), polyhexamethylene biguanidebiguandide (PHMB), a stabilized oxychloro complex, sorbic acid, and combinations thereof.
Embodiment 65 is the emulsion of any one of embodiments 1-64, wherein the emulsion is free of preservatives.
Embodiment 66 is the emulsion of any one of embodiments 1-65, wherein the emulsion has an average droplet size of from about 10 nm to 100,000 nm.
Embodiment 67 is the emulsion of any one of embodiments 1-66, wherein the emulsion has an average droplet size of 200 nm or less.
Embodiment 68 is the emulsion of any one of embodiments 1-67, wherein the emulsion remains stable for at least 6 months at 25° C.
Embodiment 69 is the emulsion of any one of embodiments 1-68, wherein the emulsion remains stable for at least 12 months at 25° C.
Embodiment 70 is the emulsion of any one of embodiments 1-69, wherein the emulsion remains stable for at least 24 months at 25° C.
Embodiment 71 is the emulsion of any one of embodiments 1-70, wherein the emulsion is formulated as an eyedrop, a cream, a gel, and ointment, a film.
Embodiment 72 is an emulsion comprising:
 about 0.005% to about 2% w/w of a multikinase inhibitor;
 about 0.1% to about 1% w/w of a poloxyl oil;
 about 0.05% to about 1% w/w of a lipophilic carrier;
 about 5% to about 15% w/w of a solubilizer; and
 water.
Embodiment 73 is the emulsion of embodiment 72, wherein the multikinase inhibitor is present in an amount from about 0.1% to about 0.5% w/w.
Embodiment 74 is the emulsion of any one of embodiments 72-73, wherein the polyoxyl oil is present in an amount from about 0.3% to about 0.7% w/w.
Embodiment 75 is the emulsion of any one of embodiments 72-74, wherein the lipophilic carrier is present in an amount from about 0.1% to about 0.5% w/w.
Embodiment 76 is the emulsion of any one of embodiments 72-75, wherein the solubilizer is present in an amount from about 8% to about 12% w/w.
Embodiment 77 is an emulsion comprising:
 about 0.1% to about 0.5% w/w of a multikinase inhibitor;
 about 0.3% to about 0.7% w/w of a polyoxyl oil;
 about 0.1% to about 0.5% w/w of a lipophilic carrier;
 about 8% to about 12% w/w of a solubilizer; and
 water.
Embodiment 78 is the emulsion of any one of embodiments 72-77, wherein the multikinase inhibitor is present in an amount of about 0.2% w/w.
Embodiment 79 is the emulsion of any one of embodiments 72-78, wherein the polyoxyl oil is present in an amount of about 0.5% w/w.
Embodiment 80 is the emulsion of any one of embodiments 72-79, wherein the lipophilic carrier is present in an amount of about 0.25% w/w.
Embodiment 81 is the emulsion of any one of embodiments 72-80, wherein the solubilizer is present in an amount of about 10% w/w.
Embodiment 82 is an emulsion comprising:
 about 0.2% w/w of a multikinase inhibitor;
 about 0.5% w/w of a polyoxyl oil;
 about 0.25% w/w of a lipophilic carrier;
 about 10% w/w of a solubilizer; and
 water.
Embodiment 83 is the emulsion of any one of embodiments 72-83, wherein the multikinase inhibitor is selected from the group consisting of afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof.
Embodiment 84 is the emulsion of any one of embodiments 72-83, wherein the multikinase inhibitor is selected from axitinib, nintedanib, and pazopanib.
Embodiment 85 is the emulsion of any one of embodiments 72-83, wherein the multikinase inhibitor is axitinib.
Embodiment 86 is the emulsion of any one of embodiments 72-83, wherein the multikinase inhibitor is nintedanib.
Embodiment 87 is the emulsion of any one of embodiments 72-83, wherein the multikinase inhibitor is pazopanib.
Embodiment 88 is the emulsion of any one of embodiments 72-87, wherein the solubilizer is a cyclic polysaccharide.
Embodiment 89 is the emulsion of embodiment 88, wherein the cyclic polysaccharide is selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof.
Embodiment 90 is the emulsion of any one of embodiments 72-89, wherein the solubilizer comprises 2-hydroxypropyl-beta-cyclodextrin.
Embodiment 91 is the emulsion of any one of embodiments 72-90, wherein the polyoxyl oil is a polyoxyl castor oil.
Embodiment 92 is the emulsion embodiment 91, wherein the polyoxyl castor oil is polyoxyl-40 castor oil, polyoxyl-35 castor oil, or a combination thereof.
Embodiment 93 is the emulsion of any one of embodiments 72-92, wherein the lipophilic carrier is selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof.
Embodiment 94 is the emulsion of any one of embodiments 72-93, wherein the lipophilic carrier comprises castor oil.
Embodiment 95 is the emulsion of any one of embodiments 72-94, further comprising a surfactant selected from the group consisting of polysorbate 20, polysorbate 40, polysorbate 60, polysorbate 80, polyoxyl-40-stearate, tocopherol, and combinations thereof.

Embodiment 96 is the emulsion of embodiment 95, wherein the surfactant is present in an amount from about 0.05% to about 5% w/w.

Embodiment 97 is the emulsion of embodiment 95, wherein the surfactant is present in an amount from about 0.1% to about 1% w/w.

Embodiment 98 is the emulsion of embodiment 95, wherein the surfactant is present in an amount of about 0.5% w/w.

Embodiment 99 is the emulsion of any one of embodiments 72-98, further comprising an additional constituent selected from the group consisting of a thickener, a buffering agent, a tonicity agent, an antioxidant, and combinations thereof.

Embodiment 100 is the emulsion of embodiment 99, wherein the thickener comprises hydroxypropyl methylcellulose, sodium carboxymethylcellulose, or a combination thereof.

Embodiment 101 is the emulsion of any one of embodiments 99-100, wherein the thickener is present in an amount from about 0.01% w/w to about 1.0% w/w.

Embodiment 102 is the emulsion of any one of embodiments 99-100, wherein the thickener is present in an amount from about 0.05% w/w to about 0.5% w/w.

Embodiment 103 is the emulsion of any one of embodiments 99-100, wherein the thickener is present in an amount of about 0.1% w/w.

Embodiment 104 is the emulsion any one of embodiments 99-103, wherein the buffering agent comprises sodium citrate.

Embodiment 105 is the emulsion of any one of embodiments 99-104, wherein the buffering agent is present in the emulsion in an amount sufficient to maintain the pH in the range of about 5.5 to about 6.5.

Embodiment 106 is the emulsion of any one of embodiments 99-105, wherein the buffering agent is present in an amount from about 0.01% w/w to about 1.0% w/w.

Embodiment 107 is the emulsion of any one of embodiments 99-105, wherein the buffering agent is present in an amount from about 0.03% w/w to about 0.06% w/w.

Embodiment 108 is the emulsion of any one of embodiments 99-105, wherein the buffering agent is present in an amount of about 0.045% w/w.

Embodiment 109 is the emulsion of any one of embodiments 99-108, wherein the antioxidant comprises edetate disodium, citric acid, or a combination thereof.

Embodiment 110 is the emulsion of any one of embodiments 99-109, wherein the antioxidant comprises edetate disodium, and the edetate disodium is present in an amount from about 0.01% w/w to about 1.0% w/w.

Embodiment 111 is the emulsion of any one of embodiments 99-109, wherein the antioxidant comprises edetate disodium, and the edetate disodium is present in an amount from about 0.05% w/w to about 0.5% w/w.

Embodiment 112 is the emulsion of any one of embodiments 99-109, wherein the antioxidant comprises edetate disodium, and the edetate disodium is present in an amount of about 0.1% w/w.

Embodiment 113 is the emulsion of any one of embodiments 99-112, wherein the antioxidant comprises citric acid, and the citric acid is present in an amount from about 0.001% to about 0.1% w/w.

Embodiment 114 is the emulsion of any one of embodiments 99-112, wherein the antioxidant comprises citric acid, and the citric acid is present in an amount from about 0.005% to about 0.05% w/w.

Embodiment 115 is the emulsion of any one of embodiments 99-112, wherein the antioxidant comprises citric acid, and the citric acid is present in an amount of about 0.015%.

Embodiment 116 is the emulsion of any one of embodiments 99-115, wherein the tonicity agent comprises glycerin.

Embodiment 117 is the emulsion of any one of embodiments 99-116, wherein the tonicity agent is present in an amount from about 0.01% w/w to about 1% w/w.

Embodiment 118 is the emulsion of any one of embodiments 99-116, wherein the tonicity agent is present in an amount from about 0.05% w/w to about 0.5% w/w.

Embodiment 119 is the emulsion of any one of embodiments 99-116, wherein the tonicity agent is present in an amount of about 0.1% w/w.

Embodiment 120 is an emulsion comprising:
  about 0.2% w/w of a multikinase inhibitor selected from the group consisting of nintedanib, axitinib, and pazopanib;
  about 0.5% w/w of a polyoxyl castor oil;
  about 0.25% w/w of castor oil;
  about 10% w/w of 2-hydroxypropyl-beta-cyclodextrin; and
  water.

Embodiment 121 is the emulsion of embodiment 120, wherein the multikinase inhibitor is axitinib.

Embodiment 122 is the emulsion of embodiment 120, wherein the multikinase inhibitor is nintedanib.

Embodiment 123 is the emulsion of embodiment 120, wherein the multikinase inhibitor is pazopanib.

Embodiment 124 is the emulsion any one of embodiments 120-123, wherein the polyoxyl castor oil is polyoxyl-40 castor oil, polyoxyl-35 castor oil, or a combination thereof.

Embodiment 125 is the emulsion of any one of embodiments 116-124, further comprising polysorbate 80 in an amount of about 0.5% w/w.

Embodiment 126 is the emulsion of any one of embodiments 120-125, further comprising hydroxypropyl methylcellulose in an amount of about 0.1% w/w.

Embodiment 127 is the emulsion any one of embodiments 120-126, further comprising sodium citrate in an amount of about 0.045% w/w.

Embodiment 128 is the emulsion of any one of embodiments 120-127, further comprising edetate disodium in an amount of about 0.1% w/w.

Embodiment 129 is the emulsion of any one of embodiments 120-128, further comprising citric acid in an amount of about 0.015%.

Embodiment 130 is the emulsion of any one of embodiments 120-129, further comprising glycerin in an amount of about 0.1% w/w.

Embodiment 131 is a method of prolonging the residence time of a multikinase inhibitor in the ocular surface comprising administering the emulsion of any one of embodiments 1-130 to an eye of a subject.

Embodiment 132 is the method of embodiment 131, wherein administering comprises applying the emulsion to the eye at least once per day.

Embodiment 133 is the method of embodiment 131, wherein administering comprises applying the emulsion to the eye at least twice per day.

Embodiment 134 is the method of embodiment 131, wherein administering comprises applying the emulsion to the eye at least three times per day.

Embodiment 135 is a method of treating an ocular condition, comprising administering the emulsion of any one of embodiments 1-130 to an eye of a subject.

Embodiment 136 is the method of embodiment 135, wherein the ocular condition is associated with angiogenesis.

Embodiment 137 is the method of embodiment 135, wherein the ocular condition is selected from the group consisting of hyperemia, neovascularization, pterygium, pinguecula, glaucoma filtration surgery and minimally invasive glaucoma surgery (MIGS), cornea transplant surgery with graft rejection, graft versus host disease, dry eye disease, atopic conjunctivitis, rosacea, ocular pemphigoid, Lyell's syndrome, Steven Johnson syndrome, viral infection (e.g. HSV-1), bacterial infection, fungal infection, parasitic infection, contact lens induced neovascularization, ulceration, alkali burns, and stem cell deficiency.

Embodiment 138 is the method of any one of embodiments 131-137, wherein the emulsion remains stable for at least 1 month at 40° C.

Embodiment 139 is the method of any one of embodiments 131-137, wherein the emulsion remains stable for at least 6 months at 40° C.

Embodiment 140 is a method of preparing the emulsion of any one of embodiments 1-130, the method comprising:
  forming a primary emulsion;
  reducing the droplet size of the primary emulsion to form a nanoemulsion;
  dissolving a multikinase inhibitor into a solution;
  combining the nanoemulsion and solution to form a nanoemulsion comprising the multikinase inhibitor; and
  optionally, filtering the nanoemulsion comprising the multikinase inhibitor.

Embodiment 141 is a method of preparing an emulsion, the method comprising:
  forming a primary emulsion;
  reducing the droplet size of the primary emulsion to form a nanoemulsion;
  dissolving a multikinase inhibitor into a solution;
  combining the nanoemulsion and solution to form a nanoemulsion comprising the multikinase inhibitor; and
  optionally, filtering the nanoemulsion comprising the multikinase inhibitor.

Embodiment 142 is the method of embodiment 140 or embodiment 141, wherein forming the primary emulsion comprises high shear mixing.

Embodiment 143 is the method of any one of embodiments 140-142, wherein reducing the droplet size comprising using a microfluidizer.

Embodiment 144 is the method of any one of embodiments 140-143, wherein filtering comprises using a 0.2-micron filter.

Embodiment 145 is the method of any one of embodiments 140-144, wherein the method further comprises filling the filtered nanoemulsion into sterile eye dropper bottles.

Embodiment 146 is the method of embodiment 145, wherein the sterile eye dropper bottles are multidose preservative free (MDPF) containers or low density polyethylene (LDPE) unit dose containers.

Embodiment 147 is the method of any one of embodiments 140-146, wherein the primary emulsion comprises:
  a polyoxyl oil;
  a lipophilic carrier; and
  water.

Embodiment 148 is the method of any one of embodiments 140-147, wherein the multikinase inhibitor is selected from afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, vemurafenib, or combinations thereof.

Embodiment 149 is the method of embodiment 148, wherein the multikinase inhibitor is selected from axitinib, nintedanib, and pazopanib.

Embodiment 150 is the method of embodiment 148, wherein the multikinase inhibitor is axitinib.

Embodiment 151 is the method of embodiment 148, wherein the multikinase inhibitor is nintedanib.

Embodiment 152 is the method of embodiment 148, wherein the multikinase inhibitor is pazopanib.

Embodiment 153 is the method of any one of embodiments 140 to 152, wherein solution further comprises a solubilizer.

Embodiment 154 is the method of embodiment 153, wherein the solubilizer is a cyclic polysaccharide.

Embodiment 155 is the method of embodiment 154, wherein the cyclic polysaccharide is selected from the group consisting of cyclodextrin, alpha-cyclodextrin, beta-cyclodextrin, gamma-cyclodextrin, 2-hydroxypropyl-alpha-cyclodextrin, 2-hydroxypropyl-beta-cyclodextrin, 2-hydroxypropyl-gamma-cyclodextrin, sulfobutyl ether-beta-cyclodextrin and combinations thereof.

Embodiment 156 is the method of any one of embodiments 147 to 155, wherein the polyoxyl oil is a polyoxyl castor oil.

Embodiment 157 is the emulsion embodiment 156, wherein the polyoxyl castor oil is polyoxyl-40 castor oil, polyoxyl-35 castor oil, or a combination thereof.

Embodiment 158 is the method of any one of embodiments 147 to 157, wherein the lipophilic carrier is selected from the group consisting of castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, medium chain triglycerides and combinations thereof.

Embodiment 159 is the method of any one of embodiments 147 to 158, wherein the primary emulsion further comprises a surfactant selected from the group consisting of polysorbate 20, polysorbate 40, polysorbate 60, polysorbate 80, polyoxyl-40-stearate, tocopherol, and combinations thereof.

Embodiment 160 is the method of any one of embodiments 147-159, wherein the multikinase inhibitor is nintedanib, the solubilizer is 2-hydroxypropyl-beta-cyclodextrin, the lipophilic carrier is castor oil, and the polyoxyl oil is polyoxyl-35 castor oil, or a combination thereof.

Embodiment 161 is the method of any one of embodiments 140 to 160, wherein the multikinase inhibitor is present in the primary emulsion an amount from about 0.001% w/w to about 10.0% w/w.

Embodiment 162 is the method of embodiment 161, wherein the multikinase inhibitor is present in the primary emulsion an amount of about 0.01% to about 1% w/w.

Embodiment 163 is the method of embodiment 161, wherein the multikinase inhibitor is present in the primary emulsion an amount of about 0.1% to about 0.5% w/w.

Embodiment 164 is the method of any one of embodiments 147 to 163, wherein the lipophilic carrier is present in the primary emulsion an amount from about 0.01% w/w to about 5.0% w/w.

Embodiment 165 is the method of embodiment 164, wherein the lipophilic carrier is present in the primary emulsion in an amount from about 0.05% to about 1% w/w.
Embodiment 166 is the method of embodiment 164, wherein the lipophilic carrier is present in the primary emulsion in an amount from about 0.1% to about 0.5% w/w.
Embodiment 167 is the method of any one of embodiments 147 to 166, wherein the polyoxyl oil is present in the primary emulsion in an amount from about 0.01% w/w to about 10% w/w.
Embodiment 168 is the method of embodiment 167, wherein the polyoxyl oil is present in the primary emulsion an amount from about 0.05% to about 1% w/w.
Embodiment 169 is the method of embodiment 167, wherein the polyoxyl oil is present in the primary emulsion an amount from about 0.1% to about 0.5% w/w.
Embodiment 170 is the method of any one of embodiments 140 to 169, wherein the primary emulsion further comprises a solubilizer, wherein the solubilizer is present in the primary emulsion in an amount from about 1% w/w to about 20% w/w.
Embodiment 171 is the method of embodiment 170, wherein the solubilizer is present in the primary emulsion in an amount from about 5% to about 15% w/w.
Embodiment 172 is the method of embodiment 170, wherein the solubilizer is present in the primary emulsion in an amount from about 8% to about 12% w/w.
Embodiment 173 is the method of any one of embodiments 147 to 172, wherein the primary emulsion further comprises an additional constituent selected from the group consisting of a thickener, a buffering agent, a tonicity agent, an antioxidant, and combinations thereof.
Embodiment 174 is the method of any one of embodiments 141-173, wherein the filtered emulsion is the emulsion of any one of embodiments 1-130.

EXAMPLES

Example 1. Emulsion Formulation Stability

Solution A and Emulsion B were prepared and stability was assessed. Solution A: 0.2% nintedanib in a solution system with 10% 2-hydroxypropyl-beta-cyclodextrin. Emulsion B: 0.5% nintedanib in an emulsion system with 5% 2-hydroxypropyl-beta-cyclodextrin, castor oil, polysorbate 80, polyoxyl-35 castor oil. Stability data at accelerated temperatures (40° C., 50° C., and 60° C.) conditions can be used to extrapolate and predict room temperature long term storage. As shown in Table 2, the multikinase inhibitor remained stable in emulsion B when stored at 40° C., 50° C., and 60° C. indicating that this formulation system could potentially maintain a 2 year shelf life, or longer, at room temperature. The typical desired room temperature shelf life for topical ocular solutions is 2 years.

Example 2: Synergistic Effect of Emulsion System of Castor Oil, Polysorbate 80, Polyoxyl-35 Castor Oil and of 2-Hydroxypropyl-Beta-Cyclodextrin to the Solubility of Nintedanib

TABLE 3

Maximum CBT-001 (nintedanib free base) Solubility in Solvents

| Solvents | Maximum solubility (mg/g) |
|---|---|
| Castor oil | 0.37 |
| 1% Polysorbate 80 | 0.25 |
| Polyoxyl-35 castor oil | 0.29 |
| 10% 2-Hydroxypropyl-beta-cyclodextrin | 2.0 |
| Maximum theoretical possible solubility of nintedanib in the mixture of castor oil, polysorbate 80, and polyoxyl-35 castor oil | 0.91 |
| Maximum theoretical possible solubility of nintedanib in the mixture of castor oil, polysorbate 80, polyoxyl-35 castor oil, and 2-hydroxypropyl-beta-cyclodextrin | 2.91 |
| Measured solubility of nintedanib in the mixture of nanoemulsion system of 0.25% castor oil, 1% castor oil, 1% polysorbate 80, and 2% polyoxyl-35-castor oil | 3.4-5.0 |
| Measured solubility of nintedanib in the mixture of 10% 2-hydroxypropyl-beta-cyclodextrin and nanoemulsion system of 0.25% castor oil, 1% polysorbate 80, and 2% polyoxyl-35 castor oil | 7.9 |

Per FDA guidance for Industry Drug Stability Guidelines, the stability of formulations can be predicted for long-term storage when it is stored at accelerated (high) temperature conditions. The stability data at accelerated temperature conditions can be used to extrapolate and predict long-term storage of drug product when stored at the recommended storage condition (ideally room temperature).

The maximum solubility of nintedanib in 10% 2-hydroxypropyl-beta-cyclodextrin was about 0.2%. The 0.2% nintedanib in 10% 2-hydroxypropyl-beta-cyclodextrin was demonstrated stable at room temperature for about 5 months and dropped below the acceptable stability specification (90% recovery) after 5 months. At the accelerated storage condition (40° C.), it was not stable at Day 4. The % recovery of nintedanib dropped below 90% on Day 4 and below 70% on Day 7. This indicates this 0.2% nintedanib in 10% 2-hydroxypropyl-beta-cyclodextrin solution may have stability issue when store for 1-2 years.

TABLE 2

| Formulation | Storage Condition | % Recovery normalized to $T_0$ | | | | | | | |
|---|---|---|---|---|---|---|---|---|---|
| | | Initial ($T_0$) | 1-Day | 4-Day | 7-Day | 14-Day | 1-M | 3-M | 5-M | 9-M |
| Solution A | 25° C. | 100.0 | NA | NA | NA | NA | 96.6 | 94.5 | 98.3 | 80.2 |
| Solution A | 40° C. | 100.0 | 100.3 | 89.2 | 68.8 | NA | NA | NA | NA | NA |
| Emulsion B | 40° C. | 100.0 | NA | NA | 97.9 | 97.3 | 99.0 | NA | NA | NA |
| Emulsion B | 50° C. | 100.0 | NA | NA | 97.3 | 98.9 | 97.4 | NA | NA | NA |
| Emulsion B | 60° C. | 100.0 | NA | NA | 93.2 | 96.2 | 95.7 | NA | NA | NA |

The 5% 2-hydroxypropyl-beta-cyclodextrin and nano-emulsion system was used to improve the concentration and stability of nintedanib in the formulation system. 0.5% nintedanib in 5% 2-hydroxypropyl-beta-cyclodextrin and a nano-emulsion system were demonstrated as stable when stored at 40° C., 50° C., and 60° C. This indicates the 5% 2-hydroxypropyl-beta-cyclodextrin and nano-emulsion system had synergetic effects on stability of nintedanib in the nano-emulsion formulation system.

The maximum solubilities of nintedanib in each solvent are listed in Table 3. A theoretical maximum possible solubility of nintedanib in the mixture can be extrapolated by assuming nintedanib is dissolved in each solvent, then each component is combined to make a mixture of all ingredients. Calculated thus the theoretical maximum possible solubility of nintedanib in the mixture would be 2.91 mg/g. Unexpectedly, in the formulation system of 10% 2-hydroxypropyl-beta-cyclodextrin and a nanoemulsion of castor oil, 1% polysorbate 80 and 2% polyoxyl-35 castor oil, an improved solubility of nintedanib was achieved at 7.9 mg/g. This indicated the 10% 2-hydroxypropyl-beta-cyclodextrin and nanoemulsion of castor oil, 1% polysorbate 80 and 2% polyoxyl-35 castor oil had synergetic effects on solubility of nintedanib.

Example 3

Solubilizers for nintedanib were investigated according to the following procedure:
1. Tare 1.5 mL Eppendorf tube
2. Add nintedanib and record weight
3. Add solubilizer and record weight
4. Add water pH 5 (except F3 & F4) and record weight
5. Beadbeater mix for 120 seconds
6. Place on rotating mixer for overnight at ambient temperature
7. Filter through 0.2 μm SPIN-X centrifuge filter
8. Measure pH of filtrate
9. Assay filtrate using CBT-001 standard solution It was surprisingly found that vastly different results were obtained for the investigated solubilizers despite many of the investigated solubilizers having similar structural properties (see, e.g., Tables 4 and 5). It was surprisingly discovered that solubilizers such as castor oil and polysorbate 80 (see, e.g., Table 3) were found to have high solubilizing performance for nintedanib.

TABLE 5

Solubility of nintedanib in various solubilizers

| Solubilizer | Nintedanib solubility (mg/g) | pH |
|---|---|---|
| BZA | 0.01 | 5.6 |
| EtOH | 0.01 | 6.1 |
| Castor oil | 0.37 | — |
| Mineral oil | 0.00 | — |
| BZK | 0.20 | 5.6 |
| polysorbate 20 | 0.06 | 6.6 |
| polysorbate 80 | 0.25 | 6.7 |
| PLXMR 188 | 0.01 | 6.5 |
| PLXMR 407 | 0.01 | 6.3 |
| PEG 400 | 0.17 | 5.6 |
| PEG 8000 | 0.01 | 6.0 |
| PG | 0.01 | 6.0 |

Various emulsion systems were identified for investigation based on the solubilizer results. It was surprisingly found that emulsion systems combining castor oil, polysorbate 80 and polyoxyl-35 castor oil can suitably solubilize nintedanib. As shown in Table 6 one of the emulsion systems can surprisingly dissolve nintedanib to about 3-5 mg/ml, an amount much greater than the previously calculated upper theoretical limit (see Table 3) for solubility of nintedanib in this combination.

TABLE 6

Solubility of nintedanib in a representative emulsion system.

| ID | F70 lot 1 | F70 lot 2 |
|---|---|---|
| Castor Oil | 1 | 1 |
| Polysorbate 80 | 1 | 1 |
| Polyoxyl-35 castor oil | 2 | 2 |
| Water | 95 | 95 |
| Nintedanib solubility | 5 | 3.4 |

Example 4

Emulsion systems were identified for developing formulations for nintedanib and other multikinase inhibitors having physical chemical properties to nintedanib.

When oil and water are mixed together, the common phenomenon after a short period of time is to form phase

TABLE 4

Compositions screened (% wt)

| % WT | F-1 | F-2 | F-3 | F-4 | F-5 | F-6 | F-7 | F-8 | F-9 | F-10 | F-11 | F-12 |
|---|---|---|---|---|---|---|---|---|---|---|---|---|
| Nintedanib | 0.5 | 0.5 | 0.5 | 0.5 | 0.5 | 0.5 | 0.5 | 0.5 | 0.5 | 0.5 | 0.5 | 0.5 |
| Benzyl alcohol | 1 | | | | | | | | | | | |
| Ethanol | | 1 | | | | | | | | | | |
| Castor oil | | | 99.5 | | | | | | | | | |
| Mineral oil | | | | 99.5 | | | | | | | | |
| BZK | | | | | 1 | | | | | | | |
| Polysorbate 20 | | | | | | 1 | | | | | | |
| Polsorbate 80 | | | | | | | 1 | | | | | |
| Poloxamer 188 | | | | | | | | 1 | | | | |
| Poloxamer 407 | | | | | | | | | 1 | | | |
| PEG 400 | | | | | | | | | | 5 | | |
| PEG 8000 | | | | | | | | | | | 2 | |
| Propylene glycol | | | | | | | | | | | | 1 |
| WFI | 98.5 | 98.5 | | | 98.5 | 98.5 | 98.5 | 98.5 | 98.5 | 94.5 | 97.5 | 98.5 | separation. Formulations with phase separation are unsuitable to use for certain ocular formulations such as eye drops. Various emulsion systems were investigated for physical stability and uniformity for potential usage in the development of ocular formulations for nintedanib and other multikinase inhibitors having similar physical chemical properties. As shown in Table 7, it was surprisingly found that some emulsion systems showed phase stability while others were not stable after three days, despite having components with similar properties. It has not been determined why some of the systems are stable while others are not stable.

The below procedure was followed for investigating physical stability of the emulsion systems:
1. Adjust 100 mL of water to pH 5
2. Tare 15 mL tube
3. Add materials and record weights
4. QS with water
5. Vortex to mix for 1 minute
6. High shear mix until a uniform emulsion is formed
7. Record appearance and pH
8. Aliquot each formulation into three 1.5 mL tubes
9. Store at −20° C., 2-8° C. & 40° C. for 3 days
10. Remove from storage and equilibrate to room temperature
11. Record appearance
12. Take only the vehicles which are uniform single-phase emulsions and transfer to centrifuge
13. Centrifuge for 10 minutes at 13K RPM.
14. Record appearance
15. Measure the pH of vehicles which are uniform single-phase emulsions determined after several rounds of testing. For example, Emulsion C showed very good stability at high temperatures (>40° C.) over several months, indicating the formulations will have good stability during long-term storage at room temperatures. These results were surprising because solution formulations were found to be unstable under the same conditions, and early emulsion formulations investigated were also found to be less stable. As illustrated in Table 8, just over half of nintedanib in the solution formulation remained after 1 month at 40° C., while nearly all nintedanib still remained in Emulsion C after 6 months under the same conditions. Table 8 also showed that Emulsion C surprisingly kept nintedanib stable for at least 3 months even at much higher temperatures of 50° C. and 60° C. These results were surprising because solution formulations were found to be unstable under the same conditions, just over half of nintedanib in the solution formulation remained after 4 weeks at 40° C., while all nintedanib still remained in Emulsion C after 6 months under the same conditions (Table 8). The same kind of emulsion system also kept axitinib, another MKI class of compound, stable for at least 3 months at 40, 50 and 60° C., indicating the likelihood of long-term stability at room temperature storage conditions (Table 9).

Method of Emulsion Formulation Development

The initial development included design, preparation and testing of multiple emulsion compositions for drug solubilization, droplet size and accelerated emulsion physical stability (size change or aggregation) evaluation. Each test composition contained the basic components including API (e.g., nintedanib), oil, surfactant(s), solubilizer, emulsifier(s), lubricant, osmotic agent and water. From the

TABLE 7

Stability results of various excipients combinations

| ID | F13 | F14 | F15 | F16 | F17 | F18 | F19 | F20 |
|---|---|---|---|---|---|---|---|---|
| Polysorbate 60 | 15 | 15 | 15 | 15 | | | | |
| Polysorbate 80 | | | | | 4 | 4 | 4 | 4 |
| ASpan 20 | 0.5 | | | | 0.5 | | | |
| GMS | | 0.5 | | | | 0.5 | | |
| Myrj 52 | | | 7 | | | | 7 | |
| Polyoxyl-35 castor oil | | | | 5 | | | | 5 |
| Castor Oil | 5 | 5 | 5 | 5 | 5 | 5 | 5 | 5 |
| Water | 79.5 | 79.5 | 73 | 75 | 90.5 | 90.5 | 84 | 86 |
| Observation of formulation on day 3 | Uniform | Separation | Uniform | Uniform | Separation | Separation | Uniform | Uniform |

Emulsion system F20 was selected as a base system for further formulation development.

Example 5

In this example, it was determined that a cyclodextrin-based solubilizer system was mixed with the selected castor oil, polysorbate 80 and polyoxyl-35 castor oil-based emulsion system, the combination was compatible and did not cause crashing out or phase separation. Furthermore, emulsion formulations containing the HP-beta-CD, castor oil, polysorbate 80, and polyoxyl-35 castor oil were found to achieve superior stability over solution formulations. Without being bound by any particular theory, it is believed that the complex interactions among the drug and all these ingredients led to this superiority over single-component formulations. This surprising finding was determined through extensive, comprehensive, and sophisticated experimentation that examined many ingredients sequentially to select the final combination. Superior compositions were initial work, 2-3 compositions were selected, modified as needed and evaluated for viscosity, osmotic pressure and emulsion physical stability. One exemplary composition was selected for additional evaluation after meeting pre-set requirements.

A pilot-scale manufacturing process was developed to produce the Prototype Formulation at 0.1-1 L batch size. The manufacturing process included: (1) dissolution of API into a primary emulsion using a high shear mixer, (2) reduction of droplet size to the size target using a microfluidizer, (3) passage of the nanoemulsion through a 0.2-micron filter, and (4) filling the nanoemulsion into sterile eye dropper bottles (Multidose Preservative Free Containers or MDPF and LDPE unit dose containers) in a biosafety hood. Batches (about 250 mL) of the Prototype Formulation were prepared at each of the 4 strengths (0, 0.05%, 0.2% and 0.5%). Using aseptic technique, Prototype Formulation batches were loaded into 5.5 mL Aptar dropper bottles (3 mL/bottle) or a LDPE unit dose container (0.3 mL/unit).

For each batch strength, formulations were tested for pH, appearance (visual and microscopic), osmotic pressure, viscosity, droplet size, API concentration and impurity. These test results were used as the initial values for the stability testing (T=0). For each batch strength, the Prototype Formulations were placed in stability chambers set at various temperatures for various time periods. Stability tests for appearance (visual and microscopic), particulate matter (count), droplet size, drug concentration, impurities/degradation products, osmolarity, and pH were performed at selected time points.

Formulations Emulsion C, F134, and F135 were prepared as follows:

Part 1: Oil/Surfactant Emulsion
1. Tare a 50 mL Falcon Tube
2. Add 1.25 g of castor oil
3. Add 0.250 g of tween 80
4. Add 0.250 g of polyoxyl-35 castor oil
5. Heat the mixture to 50° C. in a sonicator then vortex until uniform and clear
6. Add 13.25 g of deionized water
7. Homogenize the mixture at high speed until the oil droplet size is below 100 nm.
Mixing speed: 4000 RPM
Mixing time: 30 minutes
  Emulsion C Z-Avg: 35 nm
  F-134 Z-Avg: 37 nm
  F-135 Z-Avg: 33 nm Part 2: Nintedanib, Axitinib and Pazopanib in HP-beta-CD Solution
1. Tare a 50 mL Falcon tube
2. Add 25 g of DI-water to a container. 3. While stirring add 5.0 g of HP-beta-CD and stir until completely dissolved. 4. Add 0.008 g of citric acid and stir until completely dissolved. 5. Add 0.100 g of API to the mixture
6. Sonicate the mixture for 15 minutes and vortex until dissolved completely
7. Add 0.023 g of sodium citrate to the mixture and mix until completely dissolved.
8. Add 0.050 g of trisodium EDTA to the mixture and mix until completely dissolved.
9. While stirring the mixture, slowly add 0.050 g of HPMC and mix until completely dissolved.

Part 3. Formulations Emulsion C, F134, and F135
1. Tare a 100 mL glass bottle
2. Add aqueous solution (part 2)
3. Add oil emulsion (part 1)
4. Add 5 g of deionized water
5. Add 0.05 g of glycerin to the mixture and mix well.
6. Adjust the pH to 6.0 using 1N NaOH or 1N HCL.
  Emulsion C Initial pH: 6.66 Final pH: 5.87
  F-134 Initial pH: 2.51 Final pH: 6.12
  F-135 Initial pH: 1.24 Final pH: 6.03
7. QS to 50 g of deionized water and mix Part 4. Filter and Fill
1. Aseptically filter formulations through a sterile 0.2 μm syringe filter into a sterile container
2. Aseptically fill 5 mL of formulation into 5×10 mL Type 1 glass vials
3. Cap vials with rubber septum and crimp seal
4. Store 2 vials of each formulation at 2-8, 25, 40, 50 and 60° C.
5. Monitor for ppt over 1 week Final concentrations of CBT-001 (nintedanib) and excipients in the formulations were determined for the following formulations: Solution A: 0.2% nintedanib in a solution system with 10% 2-hydroxypropyl-beta-cyclodextrin. Emulsion C: 0.2% nintedanib in an emulsion system with 10% 2-hydroxypropyl-beta-cyclodextrin, castor oil, polysorbate 80, polyoxyl-35 castor oil.

TABLE 8

Accelerated in-lab stability of Emulsion C in comparison to Solution A. The percentage of remaining nintedanb is shown at each time point.

| Formulation | Storage Condition | Initial ($T_0$) | % Recovery normalized to $T_0$ | | | | |
|---|---|---|---|---|---|---|---|
| | | | 14-Day | 1-M | 3-M | 5 or 6-M | 9-M |
| Solution A | 25° C. | 100.0 | NA | 101.1 | 98.2 | 94.9* | 81.2 |
| Solution A | 40° C. | 100.0 | NA | 55.2 | 62.1 | 69.6* | NA |
| Emulsion C | 25° C. | 100.0 | 101.4 | 99.9 | 99.1 | 103.3^ | |
| Emulsion C | 40° C. | 100.0 | 101.2 | 100.9 | 105.0 | 112.0^ | NA |
| Emulsion C | 50° C. | 100.0 | 101.8 | 101.4 | 110.7 | NA | NA |
| Emulsion C | 60° C. | 100.0 | 100.7 | 101.0 | 113.9 | NA | NA |

*5 month; ^6 month

In addition to nintedanib, another multikinase inhibitor, axitinib, was investigated and surprisingly showed good stability at high temperatures over 3 months in a similar emulsion (Table 9). The experiment showed that multikinase inhibitors with similar physical and chemical properties, e.g., nintedanib and axitinib can be formulated in certain similar emulsion formulations for long-term storage.

TABLE 9

Accelerated in-lab stability of axitinib in a representative emulsion (F134). The percentage of remaining axitinib is shown at each time point.

| Formulation | Temp | Day 1 ($T_0$) | Week 2 | Week 4 | Week 8 | Week 12 |
|---|---|---|---|---|---|---|
| F134 (axitinib emulsion) | 40° C. | 100 | 97.9 | 100.3 | 98.3 | 105.1 |
| | 50° C. | 100 | 99.7 | 101.8 | 99.5 | 112.9 |
| | 60° C. | 100 | 102.8 | 102.5 | 100.0 | 114.0 |

Example 6

Emulsion formulations, used at the same strength, are superior to a solution formulation in terms of efficacy and ocular pharmacokinetic profiles in a rabbit model of corneal neovascularization (CNV) while emulsion formulation and solution formulation share similar safety profile. The solution formulation used in the study had already been shown to be safe and efficacious in a human clinical trial.

Study Summary

The study evaluated efficacy of emulsion and solution formulations in the inhibition of hyperemia and neovascularization in the corneal suture rabbit model following 7 days of topical ocular BID (twice daily) dosing of 0.2% nintedanib Emulsion, 0.05% axitinib Emulsion and 0.1% pazopanib Emulsion or TID (three times daily) dosing of 0.2% nintedanib Solution and vehicle Emulsion. The solution was the solution described in Example 5. The emulsion was very similar to Emulsion C in Example 5. In addition, the systemic and ocular pharmacokinetics and ocular tolerability were evaluated in these animals.

Figure 2:
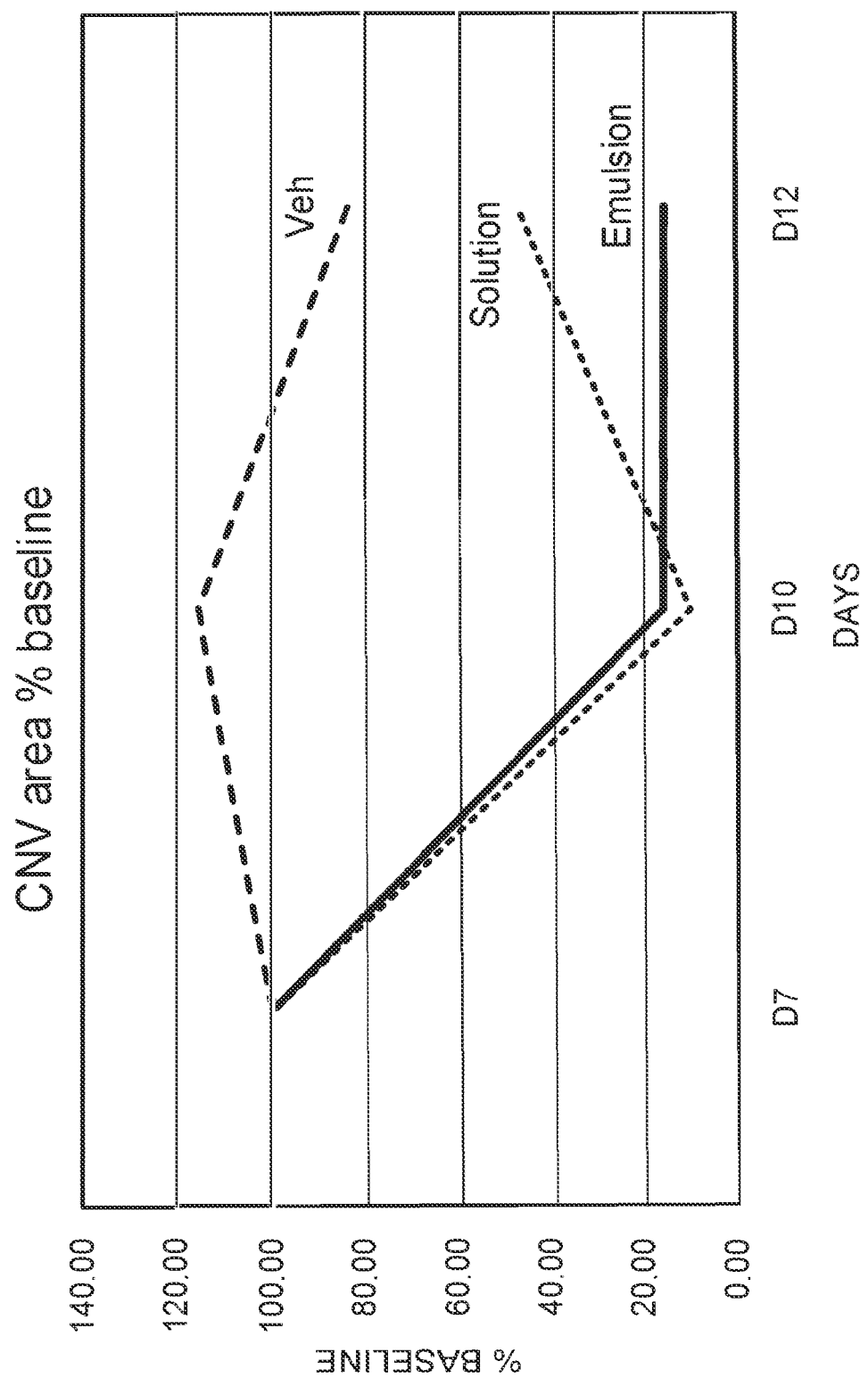
FIG. 2 is a plot showing reduction of CNV in rabbit by 0.2% nintedanib emulsion or solution according to Example 6.

All the formulations tested were well tolerated in the eye and systemically. Even though rabbits were dosed less frequently at twice a day (BID) with 0.2% nintedanib emulsion compared to three times a day (TID) with 0.2% nintedanib solution, the 0.2% nintedanib emulsion BID surprisingly showed similar or better efficacy than the 0.2% nintedanib solution, TID, as shown in FIG. 2. At Day 10, the efficacy of the emulsion and solution are similar. At Day 12, the emulsion was statistically more effective than the solution (p=0.0025).

The ocular pharmacokinetic profile indicated that the emulsion can deliver more drug to the target tissues of conjunctiva and cornea with higher $C_{max}$ and AUC (Table 10). A further analysis of the concentration/IC50 ratio over time indicates that the emulsion can have more effective inhibition of the target VEGFR2 since a ratio >10 would almost completely inhibit the target (Table 11). This demonstrated 0.2% nintedanib emulsion is superior than 0.2% nintedanib solution on delivering more drugs to the ocular surface to achieve better efficacy and longer duration.

TABLE 10

PK comparison between the nintedanib emulsion and solution
Solution vs emulsion formulations PK comparison

|  |  | $C_{max}$ (ng/g) | $T_{max}$ (hr) | $AUC_{0-tlast}$ (ng*h/g) |
|---|---|---|---|---|
| Conjunctiva | 0.2% solution TID | 438 ± 82 | 0.5 | 1620 |
|  | 0.2% emulsion BID | 763 ± 170 | 0.5 | 3982 |
| Cornea | 0.2% solution TID | 704 ± 884 | 0.5 | 3982 |
|  | 0.2% emulsion BID | 1142 ± 326 | 0.5 | 8316 |

TABLE 11

Concentration/VEGFR2 $IC_{50}$ ratio of
the two nintedanib formulations
Concentration/VEGFR2 IC50 ratio

|  | Time (h) | 0.5 | 2 | 6 | 12 |
|---|---|---|---|---|---|
| Conjunctiva | 0.2% solution TID | 38.6 | 23.6 | 5.6 | 3.7 |
|  | 0.2% emulsion BID | 67.3 | 48.2 | 19.1 | 18.5 |
| Cornea | 0.2% solution TID | 42.4 | 53.4 | 62.1 | 8.5 |
|  | 0.2% emulsion BID | 100.7 | 62.6 | 70.0 | 36.8 |

Example 7

The effectiveness of the surfactants PEG40 Stearate and polyoxyl-35 castor oil was investigated for performance in the emulsion systems. The compositions investigated are shown in Table 12.

TABLE 12

Composition of formulations F70 and F72.

|  | F70 | F72 |
|---|---|---|
| CB T001 (mg/mL) | 10 | 10 |
| Castor Oil | 1 | 1 |
| Polysorbate 80 | 1 | 1 |
| PEG40 Stearate |  | 2 |
| Polyoxyl-35 castor oil | 2 |  |
| HP-beta-CD |  |  |
| Water | 95 | 95 |

Formulations F70 and F72 (Table 12) were prepared and investigated as follows.
1. Adjust the pH 100 mL of water to pH2.0 with 1N HCL pH.
2. Label 15 mL conical tube.
3. Tare conical tube.
4. Add water and record weight.
5. Vortex into a clear solution.
6. Add Tween 80 & Polyoxyl-35 castor oil or PEG40 Stearate and record weight.
7. Add castor oil and record weight.
8. Vortex for 1 minute.
9. High shear mix into a clear or uniform solution.
10. Add API.
11. Place conical tube in an ice bath.
12. High shear mix for 30 minutes.
13. After 30 minutes, centrifuge to force non-dissolved API to bottom of tube.
14. Collect 50 µL from top of emulsion and test dropt size by LLS.
15. If greater than 200 nm, continue high shear mixing and retest.
16. Record final droplet size.
17. Measure pH.
18. If below pH 6 then adjust pH to 6 with 1N NaOH. If pH between 6-8, do not adjust.
19. Filter through 0.2 µm syringe filter.
20. Measure pH, particle size of filtrate.
21. Assay using CBT-001 (nintedanib) standard solution.

The results of this experiment are shown in Table 13. Because a higher concentration of nintedanib was achieved in formulation F70 than in formulation F72, the combination of Polyoxyl-35 castor oil and Polysorbate 80 is believed to be a better surfactant system compared to the combination of PEG40 Stearate and Polysorbate 80 for emulsifying castor oil to dissolve nintedanib.

TABLE 13

| | Results | |
|---|---|---|
| F | F70 | F72 |
| Nintedanib concentration (mg/mL) | 5.2 | 1.5 |

What is claimed is:
1. An emulsion comprising:
   about 0.2% w/w of nintedanib or about 0.1% w/w of nintedanib;
   about 0.5% w/w of polyoxyl-35 castor oil;
   about 0.25% w/w of castor oil;
   about 10% w/w of 2-hydroxypropyl-beta-cyclodextrin;
   about 0.5% w/w of polysorbate 80; and
   water.
2. The emulsion of claim 1, further comprising an additional constituent selected from a thickener, a buffering agent, an antioxidant, a tonicity agent, or a combination thereof.
3. The emulsion of claim 2, wherein the emulsion comprises a thickener, and wherein the thickener is present in an amount of about 0.05% to about 0.5% w/w.
4. The emulsion of claim 3, wherein the thickener comprises hydroxypropyl methylcellulose, sodium carboxymethylcellulose, or a combination thereof.
5. The emulsion of claim 2, wherein the emulsion comprises a buffering agent, and wherein the buffering agent is present in an amount of about 0.01% to about 1.0% w/w.
6. The emulsion of claim 5, wherein the buffering agent comprises sodium citrate, citric acid, or a combination thereof.
7. The emulsion of claim 2, wherein the emulsion comprises an antioxidant, and wherein the antioxidant comprises edetate di sodium present at an amount of about 0.01% to about 1.0% w/w.

8. The emulsion of claim 2, wherein the emulsion comprises a tonicity agent, and wherein the tonicity agent is present in an amount of about 0.01% to about 1.0% w/w.

9. The emulsion of claim 8, wherein the tonicity agent comprises glycerin.

* * * * *

UNITED STATES PATENT AND TRADEMARK OFFICE
CERTIFICATE OF CORRECTION

| | | |
|---|---|---|
| PATENT NO. | : 11,666,533 B2 | Page 1 of 1 |
| APPLICATION NO. | : 17/509774 | |
| DATED | : June 6, 2023 | |
| INVENTOR(S) | : Jinsong Ni, Van Dinh and Walter Tien | |

It is certified that error appears in the above-identified patent and that said Letters Patent is hereby corrected as shown below:

On the Title Page

Column 2 (Abstract), Line 5, Delete "polyolyl-35" and insert -- polyoxyl-35 --.

In the Claims

Column 40, Line 66, in Claim 7, Delete "di sodium" and insert -- disodium --.

Signed and Sealed this
First Day of August, 2023

Katherine Kelly Vidal
*Director of the United States Patent and Trademark Office*